US011939550B2

(12) United States Patent
Wilkinson et al.

(10) Patent No.: US 11,939,550 B2
(45) Date of Patent: Mar. 26, 2024

(54) BORATED DETERGENTS AND THEIR LUBRICATING APPLICATIONS

(71) Applicant: Infineum International Limited, Oxford (GB)

(72) Inventors: Thomas Daniel Wilkinson, Abingdon (GB); Oliver Delamore, Abingdon (GB); Alexander Coxon, Abingdon (GB); Marcus Popowicz, Abingdon (GB); Ara Samonte, Abingdon (GB); Mallika Rana, Abingdon (GB)

(73) Assignee: Infineum International Limited, Abingdon (GB)

( * ) Notice: Subject to any disclaimer, the term of this patent is extended or adjusted under 35 U.S.C. 154(b) by 0 days.

(21) Appl. No.: 18/061,145

(22) Filed: Dec. 2, 2022

(65) Prior Publication Data
US 2023/0183593 A1 Jun. 15, 2023

(30) Foreign Application Priority Data
Dec. 9, 2021 (EP) .................................... 21213439

(51) Int. Cl.
*C10M 139/00* (2006.01)
*C07C 65/10* (2006.01)
*C10M 169/04* (2006.01)
*C10N 30/00* (2006.01)
*C10N 30/04* (2006.01)
*C10N 30/10* (2006.01)

(52) U.S. Cl.
CPC .......... *C10M 139/00* (2013.01); *C07C 65/10* (2013.01); *C10M 169/04* (2013.01); *C10M 2203/003* (2013.01); *C10M 2227/061* (2013.01); *C10N 2030/041* (2020.05); *C10N 2030/10* (2013.01); *C10N 2030/43* (2020.05); *C10N 2030/52* (2020.05)

(58) Field of Classification Search
CPC ................ C07C 65/10; C10N 2030/52; C10N 2030/041; C10N 2030/43; C10N 2030/10; C10M 139/00; C10M 169/04; C10M 2203/003; C10M 2227/061
See application file for complete search history.

(56) References Cited

U.S. PATENT DOCUMENTS

| | | |
|---|---|---|
| 1,815,022 A | 7/1931 | Davis |
| 2,015,748 A | 10/1935 | Frolich |
| 2,191,498 A | 2/1940 | Reiff |
| 2,387,501 A | 10/1945 | Dietrich |
| 2,655,479 A | 10/1953 | Munday et al. |
| 2,666,746 A | 1/1954 | Munday et al. |
| 2,719,125 A | 9/1955 | Roberts |
| 2,719,126 A | 9/1955 | Fields et al. |
| 2,721,877 A | 10/1955 | Popkin et al. |
| 2,721,878 A | 10/1955 | Popkin |
| 2,760,933 A | 8/1956 | Fields et al. |
| 2,836,564 A | 5/1958 | Roberts et al. |
| 3,087,937 A | 4/1963 | Tesi et al. |
| 3,250,715 A | 5/1966 | Wyman |
| 3,254,025 A | 5/1966 | Le Seur |
| 3,502,677 A | 3/1970 | Le Seur |
| 3,663,561 A | 5/1972 | Blaha |
| 4,259,194 A | 3/1981 | deVries et al. |
| 4,259,195 A | 3/1981 | King et al. |
| 4,261,843 A | 4/1981 | King et al. |
| 4,263,152 A | 4/1981 | King et al. |
| 4,265,773 A | 5/1981 | deVries et al. |
| 4,272,387 A | 6/1981 | King et al. |
| 4,283,295 A | 8/1981 | deVries et al. |
| 4,285,822 A | 8/1981 | deVries et al. |
| 4,539,126 A | 9/1985 | Bleeker et al. |
| 4,702,850 A | 10/1987 | Gutierrez et al. |
| 4,798,684 A | 1/1989 | Salomon |
| 4,857,214 A | 8/1989 | Papay et al. |
| 4,873,009 A | 10/1989 | Anderson |
| 5,084,197 A | 1/1992 | Galic et al. |
| 5,840,663 A | 11/1998 | Nibert et al. |
| 6,599,867 B2 * | 7/2003 | Hammond ........... C10M 159/22 508/460 |
| 8,048,833 B2 | 11/2011 | Habeeb et al. |
| 10,584,300 B2 | 3/2020 | Hartley et al. |
| 10,731,101 B2 | 8/2020 | Delamore et al. |
| 2009/0005277 A1 | 1/2009 | Watts et al. |
| 2015/0005208 A1 | 1/2015 | Yaguchi et al. |
| 2017/0369808 A1 | 12/2017 | Kusuhara |

FOREIGN PATENT DOCUMENTS

| | | |
|---|---|---|
| EP | 2813563 A1 | 12/2014 |
| EP | 2878659 A1 | 6/2015 |
| WO | 94/06897 A1 | 3/1994 |

OTHER PUBLICATIONS

European Search Application 21213439.9.

* cited by examiner

*Primary Examiner* — Vishal V Vasisth

(57) ABSTRACT

Disclosed herein is an overbased alkaline earth metal hydrocarbyl-substituted salicylate detergent comprising both carbonate and borate moieties and exhibiting the following characteristics: a basicity index of at least 3.8; a ratio of soap content to mass % boron is greater than 55 mmol/kg; a soap content of at least 330 mmol/kg; a TBN, measured according to ASTM D2896, of at least 220 mg KOH/g; and a mass ratio of borate to carbonate from 0.75 to 6.0, wherein the alkaline earth metal comprises calcium and/or magnesium, and the hydrocarbyl substitution comprises 9 to 30 carbon atoms. Methods of making the boron-containing salicylate detergent, specifically to be package-stable, are also disclosed, as well as package-stable lubricant additive package concentrates and lubricating oil compositions containing same.

21 Claims, No Drawings

BORATED DETERGENTS AND THEIR LUBRICATING APPLICATIONS

PRIORITY

This invention claims priority from European Patent Application EP 21213439.9, filed Dec. 9, 2021, in the European Patent Office.

FIELD OF THE INVENTION

This disclosure relates to boron-containing detergents, generally, and borated and carbonated overbased salicylate detergents specifically. The disclosure also relates to methods of making the boron-containing detergents, preferable to be package-stable, as well as package-stable lubricant additive package concentrates and lubricating oil compositions containing such boron-containing detergents.

BACKGROUND OF THE INVENTION

Although boron can be introduced into lubricant formulations in various ways, including as associated with a detergent or as a standalone molecule, most of those formats for introducing higher amounts of boron create instabilities in additive package blending and/or formulation creation.

Conventionally, those difficulties are fewer with boron-containing dispersants. However, at anything but relatively low boron levels, using boron-containing dispersants can mean adding a large dispersant loading into an additive package or formulation, which can sometimes have negative viscometric impact on the basestock/oil, particularly as formulations move to lower viscosities. It is very difficult to add high amounts of boron even to dispersants and have that boron retain its ability to dissociate during operation and be mobile to move to a lubrication surface to assist in forming a tribofilm.

Boron-containing detergents do exist, but, even more than boron-containing dispersants, they can tend to create instabilities and have inaccessible/inactive boron in practice.

It has surprisingly been found that careful boration of certain types of detergents can yield both relatively high boron loadings, with highly accessible boron, and yet still retain relative package/formulation stability, even in known unstable situations (e.g., instabilities caused by interactions between salicylate detergents and certain organic friction modifiers).

By controlling the process of boration, as well as certain aspects of the detergent itself, stable and useful boron-containing detergents can improve additive package concentrates and formulations alike with relatively stable and accessible boron and without significant viscometric debit.

SUMMARY OF THE INVENTION

Accordingly, the present disclosure relates to an overbased alkaline earth metal hydrocarbyl-substituted salicylate detergent comprising both carbonate and borate moieties. Advantageously, the overbased alkaline earth metal hydrocarbyl-substituted salicylate detergent exhibits the following characteristics: a basicity index of at least 3.8; a ratio of soap content to mass % boron is greater than 55 mmol/kg; a soap content of at least 330 mmol/kg; a TBN, measured according to ASTM D2896, of at least 220 mg KOH/g; and a mass ratio of borate to carbonate from 0.75 to 6.0, wherein the alkaline earth metal comprises calcium and/or magnesium, and the hydrocarbyl substitution comprises 9 to 30 carbon atoms.

Additionally, or alternatively, the overbased alkaline earth metal hydrocarbyl-substituted salicylate detergent also exhibits at least three, at least four, or all five of the following: a basicity index of not greater than 9.0; a ratio of soap content to mass % boron of less than 300 mmol/kg; a TBN, measured according to ASTM D2896, of at most 500 mg KOH/g; a soap content of at most 550 mmol/kg; and a hydrocarbyl substitution comprising a $C_{14}$ to $C_{24}$ alkyl or alkenyl moiety. Further, additionally or alternatively, the overbased alkaline earth metal hydrocarbyl-substituted salicylate detergent may exhibit one or more of the following: a boron content, according to ASTM D4951, of at least 3.2% by mass; a mass ratio of borate to carbonate is from 1.0 to 5.0; an alkaline earth metal content, according to ASTM D4951, of at least 7.0% by mass; and a mass ratio of alkaline earth metal to boron is from 1.5 to 5.5. In a particular embodiment, the overbased calcium salicylate detergent exhibits all of the following: a basicity index from 5.0 to 8.3; a ratio of soap content to mass % boron between 70 and 275 mmol/kg; a TBN, measured according to ASTM D2896, from 265 to 350 mg KOH/g; a combined calcium and magnesium content, according to ASTM D4951, from 7.0% to 12.5% by mass; a boron content, according to ASTM D4951, from 3.5% to 6.8% by mass; a soap content from 350 to 520 mmol/kg; a mass ratio of alkaline earth metal to boron from 1.7 to 4.5; a mass ratio of borate to carbonate moieties from 1.6 to 3.0; and a hydrocarbyl substitution comprising a $C_{14}$ to $C_{19}$ alkyl or alkenyl moiety.

The present disclosure also relates to a method for making a substantially package-stable overbased alkaline earth metal hydrocarbyl-substituted salicylate detergent comprising both carbonate and borate moieties. The method comprises the following steps. an oil-soluble or oil-dispersible overbased but unborated alkaline earth metal hydrocarbyl-substituted salicylate detergent is provided—it has been made by reacting a mineral oil solution of an acid with a stoichiometric excess of a neutralizing agent comprising an alkaline earth metal carbonate or bicarbonate, optionally in the presence of promoter, at an elevated temperature (e.g., from 60 to 200° C.) for a sufficient period of time to have thereby formed the overbased but unborated alkaline earth metal hydrocarbyl-substituted salicylate detergent. The detergent exhibits a basicity index of at least 3.5, a soap content of at least 330 mmol/kg, an alkaline earth metal content, measured according to ASTM D4951, of at least 7.0% by mass, and a TBN, according to ASTM D2896, of at least 240 mg KOH/g. The alkaline earth metal comprises calcium and/or magnesium. The overbased but unborated alkaline earth metal hydrocarbyl-substituted salicylate detergent comprises carbonate moieties, and the hydrocarbyl substitution comprises 9 to 30 carbon atoms. This overbased but unborated alkaline earth metal hydrocarbyl-substituted salicylate detergent product is admixed in an organic diluent medium comprising an aprotic hydrocarbon solvent and a $C_1$-$C_4$ primary alcohol, optionally but preferably comprising no intentionally added water, with a boron source at a temperature below 100° C. to form a reaction mixture. The reaction mixture is heated to a temperature above 100° C. (e.g., from 105° C. to 225° C.) at a heating rate below 3° C./min in a borating process to form a crude borated detergent product. Optionally additional aprotic hydrocarbon solvent may be further added, thereby still forming a crude borated detergent product. A significant portion of the diluent medium, as well as water, formed during the borating process can be removed, in order to form the overbased alkaline earth metal hydrocarbyl-substituted salicylate detergent according to the present disclosure. In some embodiments, the aprotic hydrocarbon solvent comprises benzene, xylene, toluene, mesitylene, naphthalene, cyclohexane, cyclooctane, heptane, octane, decane, dodecane, or a combination thereof. In some embodiments, the boron source comprises orthoboric acid, metaboric acid, tetraboric acid, monoammonium borate, diammonium borate, triammonium borate, $C_1$-$C_4$ alkyl dihydrogen borate, di-$C_1$-$C_4$ alkyl hydrogen borate, tri-$C_1$-$C_4$ alkyl borate, or a combination thereof.

The present disclosure also relates to a lubricant additive package concentrate comprising: less than 40% by mass of a Group I, Group II, and/or Group III lubricating oil basestock; at least 0.5% by mass of the boron-containing overbased calcium salicylate detergent according to the present disclosure and/or made according to the method of present disclosure; at least one ashless dispersant; at least one antioxidant; at least one friction modifier; and optionally one or more of an additional detergent, a corrosion inhibitor, an antiwear agent, a seal swelling agent, an anti-foamant, an extreme pressure agent, a viscosity modifier, and a pour point depressant. The at least one friction modifier in the lubricant additive package concentrate can comprise a substantially sulfur-free ashless organic friction modifier and/or a substantially nitrogen-free and substantially sulfur-free ashless organic friction modifier. Advantageously, the lubricant additive package concentrate can exhibit package stability at ~60° C. for at least 12 weeks.

The present disclosure also relates to a lubricating oil composition comprising: at least 70% by mass of a lubricating oil basestock comprising one or more of Group I, Group II, Group III, and/or Group IV basestocks; and at least 5% by mass of the lubricant additive package concentrate according to the present disclosure.

The present disclosure also relates to a lubricating oil composition comprising: at least 85% by mass of a lubricating oil basestock comprising one or more of Group I, Group II, Group III, and/or Group IV basestocks; at least 0.05% by mass of the boron-containing overbased calcium salicylate detergent according to the present disclosure and/or made according to the method of the present disclosure; at least one ashless dispersant; at least one antioxidant; at least one friction modifier; and optionally one or more of an additional detergent, a corrosion inhibitor, an antiwear agent, a seal swelling agent, a tackifier, a demulsifier, an anti-foamant, an extreme pressure agent, a viscosity modifier, and a pour point depressant.

Although the detergents, additive package concentrates, and lubricating oil compositions described herein are disclosed as being specifically useful in engine lubricant applications, such as for passenger car motor oils (PCMO) and heavy duty diesel (HDD) engines, they may additionally or alternatively find usefulness as lubricants in other applications, such as in the powertrains of those vehicles (including transmissions), in coolant fluids for at least a portion of electrical or electronic components of a hybrid electric- or fully electric-powered powertrain, in 2-stroke and/or 4-stroke marine engine lubricants, in smaller (e.g., motorcycle, landscaping vehicle) engine lubricants, as fuel additives/addpacks/compositions in vehicles or for stationary engines, in functional (e.g., hydraulic) fluids applications, or the like.

DETAILED DESCRIPTION OF THE INVENTION

The term "comprising" or any cognate word specifies the presence of stated features, steps, integers, or components, but does not preclude the presence or addition of one or more other features, steps, integers, components, or groups thereof—it is essentially a synonym for the term "including." The expressions "consisting of" or "consisting essentially of" or cognates may be embraced within "comprising" or cognates, wherein "consists essentially of" is semi-exclusive, permitting inclusion of substances not materially affecting the characteristics of the composition to which it applies.

The term "major amount" means more than 50 mass % of a composition, such as more than 60 mass %, more than 70 mass %, from 80 to 99 mass %, or from 80 to 99.9 mass %, based upon the mass of the composition.

The term "minor amount" means 50 mass % or less of a composition; such as 40 mass % or less, 30 mass % or less, from 20 to 0.1 mass %, or from 20 to 0.001 mass %, based upon the mass of the composition.

The terms "mass %" and "% by mass" each mean mass percent of a component, based upon the mass of the composition (typically measured in grams), unless otherwise indicated, and is alternately referred to as weight percent ("weight %," "%," "% by weight," or "% w/w").

The term "active ingredient" (also referred to as "a.i." or "A.I."), such as in an additive component, refers to material that is neither diluent nor solvent/eluent.

The terms "oil-soluble" and "oil-dispersible," or cognate terms, used herein do not necessarily indicate that the compounds or additives are soluble, dissolvable, miscible, or are capable of being suspended in an oil medium in all proportions. These do mean, however, that they are, for example, relatively soluble or stably dispersible in the oil medium to an extent sufficient to exert their intended effect in the environment in which the medium is employed. Moreover, the additional incorporation of other components/additives may also permit incorporation of higher levels of a particular component/additive, if desired.

The terms "group," "moiety," and "radical," as well as cognate terms, are used interchangeably herein.

The term "hydrocarbon" means a compound of hydrogen and carbon atoms. A "heteroatom" is an atom other than carbon or hydrogen. When referred to as "hydrocarbons," particularly as "refined hydrocarbons," the hydrocarbons may also contain one or more heteroatoms or heteroatom-containing groups (such as halo, especially chloro and/or fluoro, amino, amido, alkoxyl, carbonyl, carboxyl, mercapto, alkylmercapto, nitrile, nitro, nitroso, sulfoxy, sulfonyl, etc.) in minor amounts (e.g., where the heteroatom(s) do(es) not substantially alter the hydrocarbonaceous properties of the hydrocarbon).

The term "hydrocarbyl" means a group that contains hydrogen and carbon atoms. Preferably, the group consists essentially of, more preferably consists only of, hydrogen and carbon atoms, unless specified otherwise. The term "hydrocarbyl," as used herein, includes "alkyl," "alkenyl," "alkynyl," "aryl," "alkaryl," and "aralkyl," inter alia. Hydrocarbyl groups may contain one or more heteroatoms other than carbon and hydrogen provided they do not affect the essentially hydrocarbyl nature of the group. Those skilled in the art will be aware of suitable groups (e.g., halo, especially chloro and/or fluoro, amino, amido, alkoxyl, carbonyl, carboxyl, mercapto, alkylmercapto, nitrile, nitro, nitroso, sulfoxy, sulfonyl, etc.).

The term "alkyl" means a radical of carbon and hydrogen (such as $C_1$ to $C_{30}$). Alkyl groups in a compound are typically bonded to the compound directly via a covalent bond. Unless otherwise specified, alkyl groups may be linear (unbranched), branched, cyclic, acyclic, or part cyclic/acyclic. Representative examples of aliphatic (saturated) alkyl groups include, but are not limited to, methyl, ethyl, n-propyl, iso-propyl, n-butyl, sec-butyl, iso-butyl, tert-butyl, n-pentyl, iso-pentyl, neo-pentyl, hexyl, heptyl, octyl, dimethylhexyl, nonyl, decyl, undecyl, dodecyl, tridecyl, tetradecyl, pentadecyl, hexadecyl, heptadecyl, octadecyl, nonadecyl, eicosyl, docosyl, triacontyl, and the like.

The term "alkenyl" means a radical of carbon and hydrogen (such as $C_2$ to $C_{30}$) having at least one double bond. Alkenyl groups in a compound are typically bonded to the compound directly via a covalent bond. Unless otherwise specified, alkenyl groups may be linear (unbranched), branched, cyclic, acyclic, or part cyclic/acyclic.

The term "alkylene" means bivalent hydrocarbon radical, which may be linear (unbranched), branched, cyclic, acyclic, or part cyclic/acyclic, and which typically exhibits its bivalence by being covalently bonded at two different positions within (or "ends" of) the radical. Representative examples of alkylenes include, but are not limited to, methylene, ethylene, propylene, butylene, pentylene, hexylene, heptylene, octylene, nonylene, decylene, 1-methyl ethylene, 1-ethyl ethylene, 1-ethyl-2-methyl ethylene, 1,1-dimethyl ethylene, 1-ethyl propylene, and the like.

The term "alkynyl" means a radical of carbon and hydrogen (such as $C_2$ to $C_{30}$) having at least one carbon-to-carbon triple bond.

The term "aryl" means a group containing at least one aromatic ring, such as a cyclopentadiene, phenyl, naphthyl, anthracenyl, or the like. Aryl groups can be all hydrocarbon (such as $C_5$ to $C_{40}$), although aryl groups are known to optionally also contain heteroatoms such as nitrogen (e.g., pyridines). Aryl groups may contain one or more hydrocarbyl group substitutions (if the hydrocarbyl group is "alkyl," it can be considered an "aralkyl" group herein), heteroatoms, or heteroatom-containing groups. For clarity, alkyl groups that have aryl substitutions are called "alkaryl" groups herein, whereas aryl groups that have alkyl substitutions are called "aralkyl" groups herein.

The term "substituted" means that an atom (typically a hydrogen atom herein) has been replaced with another moiety, such as a hydrocarbyl group, a heteroatom, or a heteroatom-containing group.

The term "halogen" or "halo" means an atom from Group 17 of the Periodic Table of Elements or a group 17 radical, such as fluoro, chloro, bromo, and/or iodo.

The term "ashless" in relation to an additive means the additive does not include a metal atom. In this context, boron is not considered a metal atom.

The term "effective amount" in respect of an additive or other functional component of a composition means an amount of such an additive/functional component, such as in a lubricating oil composition, sufficient to provide the desired functional/technical effect.

The term "ppm" means parts per million by mass, based on the total mass. The terms "wppm" or "ppm by weight" are considered interchangeable therewith.

The term "Total Base Number," also referred to as "TBN," is interchangeable with the term "Base Number," in relation to an additive component or a lubricating oil composition, for example. Unless otherwise specified, TBN is measured according to ASTM D2896 and expressed in units of mg KOH/g.

The term "Total Acid Number," also referred to as "TAN," such as with respect to an additive component or a lubricating oil composition, for example, means total acid number and is measured according to ASTM D664.

"Phosphorus content" is usually quoted in mass % or ppm and, unless otherwise stated, is measured according to ASTM D5185.

"Sulfur content" is usually quoted in mass % or ppm and, unless otherwise stated, is measured according to ASTM D2622.

"Package stability," as used herein with reference to an additive package and/or a formulation containing a combination of additive components (e.g., from dilution of an additive package), is assessed over a period of ~12 weeks. Samples are taken according to the guidelines set in ASTM D4057. Measurements are taken weekly by examining samples in graduated centrifuge tubes, e.g., of 100 mL capacity, with the first graduation not exceeding 0.05% volume. Measurements include a visual assessment of, e.g., haze, phase separation, flocculation/suspension, gelation, "fish eye," sedimentation, and waxing, inter alia. Unless otherwise noted, week 0 measurements are taken at ambient temperature (e.g., ~15° C.-30° C.), while all other weekly measurements are taken upon exposure to an oven at ~60° C.±5° C. (samples are removed from the oven temporarily to make the visual assessment, after which they are placed back into the oven until the last week 12 measurement). In certain situations (always noted), an anomalous early reading (e.g., at week 0) may be updated after ~24 hours (update usually indicated by an asterisk and a comment). Visual assessments are generally taken under both natural light and relatively high-intensity light to ensure accurate assessment. If necessary, an appropriate solvent and/or an appropriate fabric wipe may be applied to the outside of the vessel to ensure a clear view. Although acceptable package stability may be subjectively judged in certain situations, typically a package-stable composition may be evaluated indicating only either clear and bright ("CB") or slightly hazy ("SH") as visual indicator and trace sediment ("tsed"), minor sediment ("MTS"), or the absence of any sediment notation. Although some mixtures of additives (and diluent) may not be stable in additive package concentrations, they may nevertheless be stable when sufficiently diluted in formulations, i.e., "formulation stability." Formulation-stable compositions that are not package-stable may typically be less desirable, as they tend to require that some blending of additive components be done in the presence of larger amounts of diluents, and blending of package-unstable components can occasionally lead to inconsistent formulation stability and/or formulation storage stability issues.

It should be understood that various additive components used, essential as well as optimal and customary, may react under conditions of formulation, blending, storage, and/or use and that the present disclosure also encompasses a product obtainable or obtained as a result of any or all such reaction(s).

It should also be understood that any upper and lower quantity, range, and/or ratio limits set forth herein may be independently combined.

It should be further understood that disclosed elements and/or preferred features of each aspect of the present disclosure may be regarded as disclosed elements and/or as preferred features (as the case may be) of every other aspect of the present disclosure. Accordingly, disclosed elements and/or preferred (and/or advantageous) features of one aspect of the present disclosure may be independently combined with other disclosed elements and/or preferred (and/or advantageous) features of the same aspect or different aspects of the present disclosure.

Method of Making a Boron-Containing Overbased Alkaline Earth Metal Detergent

Although there are various different ways to make a boron-containing overbased alkaline earth metal detergent, it has been found that the inventive method delineated herein can advantageously result in enhanced package stability when the resultant detergent is admixed with other additives into a lubricant additive package method for making a substantially package-stable overbased alkaline earth metal hydrocarbyl-substituted salicylate detergent comprising both carbonate and borate moieties.

First, an oil-soluble or oil-dispersible overbased but unborated alkaline earth metal hydrocarbyl-substituted salicylate detergent can be provided. The unborated detergent can advantageously exhibit basicity index minima (and/or optionally maxima), soap content minima (and/or optionally maxima), calcium content minima (and/or optionally maxima), TBN minima (and/or optionally maxima), etc., e.g.: a basicity index of at least 3.5; a soap content of at least 330 mmol/kg; an alkaline earth metal content, measured according to ASTM D4951, of at least 7.0% by mass; and a TBN, according to ASTM D2896, of at least 240 mg KOH/g. The alkaline earth metal in the unborated detergent can advantageously comprise calcium and/or magnesium. The unborated detergent can advantageously comprise carbonate moieties, which (without being bound by theory) may facilitate the overbasing of the alkaline earth metal in the detergent. The hydrocarbyl substitution on the unborated detergent can comprise 9 to 30 carbon atoms.

The unborated detergent may represent a commercial unborated detergent component or it may simply be pre-made by a separate process. As such, the TBN of the unborated detergent specified above may be based on a detergent component that can have less than 100% active ingredient (e.g., having ~25-60 mass % diluent and/or non-detergent compounds), or the TBN may be calculated on the active ingredient portion of the detergent only (ignoring any diluent and/or non-detergent compounds incorporated into the detergent component). TBN values herein are typically determined on a detergent component basis (e.g., including diluent), unless otherwise specified.

Although "basicity index" in a detergent component is strictly defined as a ratio between basic and acidic compounds therein, those of ordinary skill in the art understand that, effectively, it is calculated as the equivalents ratio of the total alkaline earth metal compounds to the total of organic acid compounds, which, in a pre-formulated (optionally diluted) detergent, often equates to the molar (concentration) ratio of total alkaline earth metal to total soap. "Basicity Index" in such detergents can, therefore, interchangeably be referred to as "metal ratio."

The overbased but unborated alkaline earth metal hydrocarbyl-substituted salicylate detergent can be made by any adequate process, but preferably by one that results in the detergent containing carbonate moieties. One such exemplary process can include reacting a mineral oil solution of an acid with a stoichiometric excess of a neutralizing agent, preferably comprising an alkaline earth metal carbonate or bicarbonate, optionally in the presence of promoter, at a temperature from ~60° C. to ~200° C. for a sufficient period of time to have thereby formed the overbased but unborated alkaline earth metal hydrocarbyl-substituted salicylate detergent. The formed product may be filtered. The "promoter," when utilized in the neutralization step, may aid the incorporation of a large excess of salt/base. Examples of compounds useful as promoters may include, but are not necessarily limited to, phenolic substances such as phenol, naphthol, alkyl phenol, thiophenol, sulfurized alkylphenol, and condensation products of formaldehyde with a phenolic substance; alcohols such as methanol, 2-propanol, octanol, Cellosolve™ alcohol, Carbitol™ alcohol, ethylene glycol, stearyl alcohol, and cyclohexyl alcohol; amines such as aniline, phenylene diamine, phenothiazine, phenyl-beta-naphthylamine, and dodecylamine; and combinations thereof.

Thereafter, said overbased but unborated alkaline earth metal hydrocarbyl-substituted salicylate detergent can be admixed in an organic diluent medium with a boron source at an appropriate temperature, such as below 100° C., to form a reaction mixture. The organic diluent medium can comprise an aprotic hydrocarbon solvent and a $C_1$-$C_4$ primary alcohol, but can advantageously comprise substantially no, or no, intentionally added water. "No intentionally added water" should be understood to exclude water that may be trapped in the solvent or primary alcohol diluent, or trapped in the overbased detergent (e.g., as an impurity, as absorbed from a moist environment, or as moderately/strongly bound to moieties such as carbonates and/or alkaline earth metal ions/dipoles), as well as what may be considered, for example, process water from the boric acid decomposition, carbonate binding, and/or other elements of overbased (but unborated) detergent formation.

The aprotic hydrocarbon solvent may advantageously comprise benzene, xylene, toluene, mesitylene, naphthalene, cyclohexane, cyclooctane, heptane, octane, decane, dodecane, or a combination thereof (in particular, xylene, toluene, heptane, or a combination thereof). The boron source may advantageously comprise orthoboric acid, metaboric acid, tetraboric acid, monoammonium borate, diammonium borate, triammonium borate, $C_1$-$C_4$ alkyl dihydrogen borate, di-$C_1$-$C_4$ alkyl hydrogen borate, tri-$C_1$-$C_4$ alkyl borate, or a combination thereof (in particular, orthoboric acid, metaboric acid, $C_1$-$C_4$ alkyl dihydrogen borate, di-$C_1$-$C_4$ alkyl hydrogen borate, tri-$C_1$-$C_4$ alkyl borate, or a combination thereof). The boron source may be added as such or may be formed in situ (e.g., in the cases of $C_1$-$C_4$ alkyl dihydrogen borate, di-$C_1$-$C_4$ alkyl hydrogen borate, and tri-$C_1$-$C_4$ alkyl borate, the $C_1$-$C_4$ primary alcohol in the medium may at least partially react with orthoboric and/or metaboric acid, for example, to provide an in situ reacted boron source).

The boron- and detergent-containing reaction mixture may then be heated to a sufficiently high temperature, e.g., from above 100° C. to 275° C. or from 105° C. to 225° C., at a sufficiently gentle heating rate, e.g., below 5° C./min, below 3° C./min, or below 2° C./min, in a borating process to form a crude borated detergent product. Optionally, in some embodiments, additional aprotic hydrocarbon solvent may be added, e.g., to make up for originally loaded aprotic hydrocarbon solvent that may have evaporated due to the elevated reaction temperatures. Even if additional solvent is added, the mixture still is treated as forming a crude borated detergent product.

Thereafter, a significant portion of the diluent medium, as well as water, that is formed during the borating process can be removed, e.g., by known purification techniques such as elevated temperature/reduced pressure evaporation of volatiles, product phase separation/crystallization and washing, or the like, in order to form the overbased and borated alkaline earth metal hydrocarbyl-substituted salicylate detergent according to the present disclosure.

Without being bound by theory, although it may be possible for the reaction that introduces the carbonate moieties into the detergent, thereby enabling the overbasing of the alkaline earth metal in the detergent, to occur in a coterminous step, the present disclosure specifies that the carbonating/alkaline earth metal overbasing step is separate from, and occurs prior to, the step of introducing boron to (e.g., borating). Even a step that creates a neutral or alkaline earth metal pre-loaded detergent, followed by a step where boron is introduced simultaneously to alkaline earth metal content being deliberately increased through additional carbonation/alkaline earth metal inclusion, is still distinct from the separate, ordered steps of first carbonating/loading with alkaline earth metal and second borating (introducing boron-containing species into the already overbased product of the first step. It is believed to be advantageous, according to the present disclosure, for the alkaline earth metal loading and boron-introducing steps to be separate and sequentially ordered, e.g., to attain one or more (unexpectedly) desirable outcome(s) in alkaline earth metal retention, boron retention, detergent/component stability, additive detergency, down-the-line detergent-containing additive package stability, further-down-the-line detergent-containing formulation stability, detergent-containing formulation performance as-loaded, and/or detergent-containing formulation performance over time, inter alia.

Boron-Containing Overbased Alkaline Earth Metal Detergents

Boron-containing overbased alkaline earth metal hydrocarbyl-substituted salicylate detergents according to the present disclosure comprise both carbonate moieties from the alkaline earth metal overbasing and borate moieties. They may also be made according to methods described in the present disclosure. Boron-containing overbased alkaline earth metal hydrocarbyl-substituted salicylate detergents according to the present disclosure advantageously exhibit one or more, two or more, three or more, four or more, five or more, six or more, seven or more, eight or more, or all nine of the following characteristics.

Basicity Index (metal ratio). Boron-containing overbased salicylate detergents according to the present invention can have a basicity index of at least 3.5, e.g., at least 3.6, at least 3.8; at least 4.0, at least 4.3, at least 4.7, at least 5.0, at least 5.3, or at least 5.7, and/or a basicity index not greater than 12, e.g., not greater than 10, not greater than 9.5, not greater than 9.0, not greater than 8.8, not greater than 8.5, not greater than 8.3, or not greater than 8.0. Thus, the basicity index can be from 3.5 to 12, from 3.5 to 10, from 3.5 to 9.5, from 3.5 to 9.0, from 3.5 to 8.8, from 3.5 to 8.5, from 3.5 to 8.3, from 3.5 to 8.0, from 3.6 to 12, from 3.6 to 10, from 3.6 to 9.5, from 3.6 to 9.0, from 3.6 to 8.8, from 3.6 to 8.5, from 3.6 to 8.3, from 3.6 to 8.0, from 3.8 to 12, from 3.8 to 10, from 3.8 to 9.5, from 3.8 to 9.0, from 3.8 to 8.8, from 3.8 to 8.5, from 3.8 to 8.3, from 3.8 to 8.0, from 4.0 to 12, from 4.0 to 10, from 4.0 to 9.5, from 4.0 to 9.0, from 4.0 to 8.8, from 4.0 to 8.5, from 4.0 to 8.3, from 4.0 to 8.0, from 4.3 to 12, from 4.3 to 10, from 4.3 to 9.5, from 4.3 to 9.0, from 4.3 to 8.8, from 4.3 to 8.5, from 4.3 to 8.3, from 4.3 to 8.0, from 4.7 to 12, from 4.7 to 10, from 4.7 to 9.5, from 4.7 to 9.0, from 4.7 to 8.8, from 4.7 to 8.5, from 4.7 to 8.3, from 4.7 to 8.0, from 5.0 to 12, from 5.0 to 10, from 5.0 to 9.5, from 5.0 to 9.0, from 5.0 to 8.8, from 5.0 to 8.5, from 5.0 to 8.3, from 5.0 to 8.0, from 5.3 to 12, from 5.3 to 10, from 5.3 to 9.5, from 5.3 to 9.0, from 5.3 to 8.8, from 5.3 to 8.5, from 5.3 to 8.3, from 5.3 to 8.0, from 5.7 to 12, from 5.7 to 10, from 5.7 to 9.5, from 5.7 to 9.0, from 5.7 to 8.8, from 5.7 to 8.5, from 5.7 to 8.3, or from 5.7 to 8.0 (in particular, the basicity index can be at least 3.8, at least 5.0, not greater than 9.0, from 3.8 to 9.0, or from 5.0 to 8.3).

Soap content. Boron-containing overbased salicylate detergents according to the present invention can have a soap content of at least 300 mmol/kg, e.g., at least 320 mmol/kg, at least 330 mmol/kg, at least 350 mmol/kg, at least 370 mmol/kg, at least 390 mmol/kg, at least 400 mmol/kg, or at least 420 mmol/kg, and/or a soap content of at most 600 mmol/kg, e.g., at most 570 mmol/kg, at most 550 mmol/kg, at most 530 mmol/kg, at most 520 mmol/kg, at most 500 mmol/kg, or at most 480 mmol/kg. Thus, the soap content can be from 300 mmol/kg to 600 mmol/kg, from 300 mmol/kg to 570 mmol/kg, from 300 mmol/kg to 550 mmol/kg, from 300 mmol/kg to 530 mmol/kg, from 300 mmol/kg to 520 mmol/kg, from 300 mmol/kg to 500 mmol/kg, from 300 mmol/kg to 480 mmol/kg, from 320 mmol/kg to 600 mmol/kg, from 320 mmol/kg to 570 mmol/kg, from 320 mmol/kg to 550 mmol/kg, from 320 mmol/kg to 530 mmol/kg, from 320 mmol/kg to 520 mmol/kg, from 320 mmol/kg to 500 mmol/kg, from 320 mmol/kg to 480 mmol/kg, from 330 mmol/kg to 600 mmol/kg, from 330 mmol/kg to 570 mmol/kg, from 330 mmol/kg to 550 mmol/kg, from 330 mmol/kg to 530 mmol/kg, from 330 mmol/kg to 520 mmol/kg, from 330 mmol/kg to 500 mmol/kg, from 330 mmol/kg to 480 mmol/kg, from 350 mmol/kg to 600 mmol/kg, from 350 mmol/kg to 570 mmol/kg, from 350 mmol/kg to 550 mmol/kg, from 350 mmol/kg to 530 mmol/kg, from 350 mmol/kg to 520 mmol/kg, from 350 mmol/kg to 500 mmol/kg, from 350 mmol/kg to 480 mmol/kg, from 370 mmol/kg to 600 mmol/kg, from 370 mmol/kg to 570 mmol/kg, from 370 mmol/kg to 550 mmol/kg, from 370 mmol/kg to 530 mmol/kg, from 370 mmol/kg to 520 mmol/kg, from 370 mmol/kg to 500 mmol/kg, from 370 mmol/kg to 480 mmol/kg, from 390 mmol/kg to 600 mmol/kg, from 390 mmol/kg to 570 mmol/kg, from 390 mmol/kg to 550 mmol/kg, from 390 mmol/kg to 530 mmol/kg, from 390 mmol/kg to 520 mmol/kg, from 390 mmol/kg to 500 mmol/kg, from 390 mmol/kg to 480 mmol/kg, from 400 mmol/kg to 600 mmol/kg, from 400 mmol/kg to 570 mmol/kg, from 400 mmol/kg to 550 mmol/kg, from 400 mmol/kg to 530 mmol/kg, from 400 mmol/kg to 520 mmol/kg, from 400 mmol/kg to 500 mmol/kg, from 400 mmol/kg to 480 mmol/kg, from 420 mmol/kg to 600 mmol/kg, from 420 mmol/kg to 570 mmol/kg, from 420 mmol/kg to 550 mmol/kg, from 420 mmol/kg to 530 mmol/kg, from 420 mmol/kg to 520 mmol/kg, from 420 mmol/kg to 500 mmol/kg, or from 420 mmol/kg to 480 mmol/kg (in particular, the soap content can be at least 330 mmol/kg, at least 370 mmol/kg, at most 550 mmol/kg, from 350 mmol/kg to 520 mmol/kg, or from 370 mmol/kg to 500 mmol/kg).

Ratio of soap content to mass % boron. Boron-containing overbased salicylate detergents according to the present invention can have a ratio of soap content to mass % boron of greater than 50 mmol/kg, e.g., greater than 55 mmol/kg, greater than 58 mmol/kg, greater than 61 mmol/kg, greater than 64 mmol/kg, greater than 67 mmol/kg, or greater than 70 mmol/kg, and/or a ratio of soap content to mass % boron of less than 300 mmol/kg, e.g., less than 275 mmol/kg, less than 250 mmol/kg, less than 225 mmol/kg, less than 200 mmol/kg, less than 175 mmol/kg, or less than 150 mmol/kg. Thus, the ratio of soap content to mass % boron can be between 50 mmol/kg and 300 mmol/kg, between 50 mmol/kg and 275 mmol/kg, between 50 mmol/kg and 250 mmol/kg, between 50 mmol/kg and 225 mmol/kg, between 50 mmol/kg and 200 mmol/kg, between 50 mmol/kg and 175 mmol/kg, between 50 mmol/kg and 150 mmol/kg, between 55 mmol/kg and 300 mmol/kg, between 55 mmol/kg and 275 mmol/kg, between 55 mmol/kg and 250 mmol/kg, between 55 mmol/kg and 225 mmol/kg, between 55 mmol/kg and 200 mmol/kg, between 55 mmol/kg and 175 mmol/kg, between 55 mmol/kg and 150 mmol/kg, between 58 mmol/kg and 300 mmol/kg, between 58 mmol/kg and 275 mmol/kg, between 58 mmol/kg and 250 mmol/kg, between 58 mmol/kg and 225 mmol/kg, between 58 mmol/kg and 200 mmol/kg, between 58 mmol/kg and 175 mmol/kg, between 58 mmol/kg and 150 mmol/kg, between 61 mmol/kg and 300 mmol/kg, between 61 mmol/kg and 275 mmol/kg, between 61 mmol/kg and 250 mmol/kg, between 61 mmol/kg and 225 mmol/kg, between 61 mmol/kg and 200 mmol/kg, between 61 mmol/kg and 175 mmol/kg, between 61 mmol/kg and 150 mmol/kg, between 64 mmol/kg and 300 mmol/kg, between 64 mmol/kg and 275 mmol/kg, between 64 mmol/kg and 250 mmol/kg, between 64 mmol/kg and 225 mmol/kg, between 64 mmol/kg and 200 mmol/kg, between 64 mmol/kg and 175 mmol/kg, between 64 mmol/kg and 150 mmol/kg, between 67 mmol/kg and 300 mmol/kg, between 67 mmol/kg and 275 mmol/kg, between 67 mmol/kg and 250 mmol/kg, between 67 mmol/kg and 225 mmol/kg, between 67 mmol/kg and 200 mmol/kg, between 67 mmol/kg and 175 mmol/kg, between 67 mmol/kg and 150 mmol/kg, between 70 mmol/kg and 300 mmol/kg, between 70 mmol/kg and 275 mmol/kg, between 70 mmol/kg and 250 mmol/kg, between 70 mmol/kg and 225 mmol/kg, between 70 mmol/kg and 200 mmol/kg, between 70 mmol/kg and 175 mmol/kg, or between 70 mmol/kg and 150 mmol/kg (in particular, the ratio of soap content to mass % boron can be greater than 55 mmol/kg, less than 300 mmol/kg, between 55 mmol/kg and 300 mmol/kg, between 70 and 275 mmol/kg, or between 55 mmol/kg and 200 mmol/kg).

Total base number (TBN), measured according to ASTM D2896. Boron-containing overbased salicylate detergents according to the present invention can have a TBN of at least 220 mg KOH/g, e.g., at least 235 mg KOH/g, at least 250 mg KOH/g, at least 265 mg KOH/g, or at least 280 mg KOH/g, and/or a TBN of at most 500 mg KOH/g, e.g., at most 470 mg KOH/g, at most 440 mg KOH/g, at most 410 mg KOH/g, at most 380 mg KOH/g, at most 350 mg KOH/g, or at most 320 mg KOH/g. Thus, the TBN can be from 220 mg KOH/g to 500 mg KOH/g, from 220 mg KOH/g to 470 mg KOH/g, from 220 mg KOH/g to 440 mg KOH/g, from 220 mg KOH/g to 410 mg KOH/g, from 220 mg KOH/g to 380 mg KOH/g, from 220 mg KOH/g to 350 mg KOH/g, from 220 mg KOH/g to 320 mg KOH/g, from 235 mg KOH/g to 500 mg KOH/g, from 235 mg KOH/g to 470 mg KOH/g, from 235 mg KOH/g to 440 mg KOH/g, from 235 mg KOH/g to 410 mg KOH/g, from 235 mg KOH/g to 380 mg KOH/g, from 235 mg KOH/g to 350 mg KOH/g, from 235 mg KOH/g to 320 mg KOH/g, from 250 mg KOH/g to 500 mg KOH/g, from 250 mg KOH/g to 470 mg KOH/g, from 250 mg KOH/g to 440 mg KOH/g, from 250 mg KOH/g to 410 mg KOH/g, from 250 mg KOH/g to 380 mg KOH/g, from 250 mg KOH/g to 350 mg KOH/g, from 250 mg KOH/g to 320 mg KOH/g, from 265 mg KOH/g to 500 mg KOH/g, from 265 mg KOH/g to 470 mg KOH/g, from 265 mg KOH/g to 440 mg KOH/g, from 265 mg KOH/g to 410 mg KOH/g, from 265 mg KOH/g to 380 mg KOH/g, from 265 mg KOH/g to 350 mg KOH/g, from 265 mg KOH/g to 320 mg KOH/g, from 280 mg KOH/g to 500 mg KOH/g, from 280 mg KOH/g to 470 mg KOH/g, from 280 mg KOH/g to 440 mg KOH/g, from 280 mg KOH/g to 410 mg KOH/g, from 280 mg KOH/g to 380 mg KOH/g, from 280 mg KOH/g to 350 mg KOH/g, or from 280 mg KOH/g to 320 mg KOH/g (in particular, the TBN can be at least 220 mg KOH/g, at most 500 mg KOH/g, from 235 mg KOH/g to 440 mg KOH/g, or from 265 mg KOH/g to 350 mg KOH/g).

Boron content, according to ASTM D4951. Boron-containing overbased salicylate detergents according to the present invention can have a boron content of at least 3.0% by mass, e.g., at least 3.2% by mass, at least 3.4% by mass, at least 3.5% by mass, at least 3.6% by mass, or at least 3.7% by mass, and/or a boron content of at most 7.0% by mass, at most 6.8% by mass, at most 6.6% by mass, at most 6.4% by mass, at most 6.2% by mass, or at most 6.0% by mass. Thus, the boron content can be from 3.0% by mass to 7.0% by mass, from 3.0% by mass to 6.8% by mass, from 3.0% by mass to 6.6% by mass, from 3.0% by mass to 6.4% by mass, from 3.0% by mass to 6.2% by mass, from 3.0% by mass to 6.0% by mass, from 3.2% by mass to 7.0% by mass, from 3.2% by mass to 6.8% by mass, from 3.2% by mass to 6.6% by mass, from 3.2% by mass to 6.4% by mass, from 3.2% by mass to 6.2% by mass, from 3.2% by mass to 6.0% by mass, from 3.4% by mass to 7.0% by mass, from 3.4% by mass to 6.8% by mass, from 3.4% by mass to 6.6% by mass, from 3.4% by mass to 6.4% by mass, from 3.4% by mass to 6.2% by mass, from 3.4% by mass to 6.0% by mass, from 3.5% by mass to 7.0% by mass, from 3.5% by mass to 6.8% by mass, from 3.5% by mass to 6.6% by mass, from 3.5% by mass to 6.4% by mass, from 3.5% by mass to 6.2% by mass, from 3.5% by mass to 6.0% by mass, from 3.6% by mass to 7.0% by mass, from 3.6% by mass to 6.8% by mass, from 3.6% by mass to 6.6% by mass, from 3.6% by mass to 6.4% by mass, from 3.6% by mass to 6.2% by mass, from 3.6% by mass to 6.0% by mass, from 3.7% by mass to 7.0% by mass, from 3.7% by mass to 6.8% by mass, from 3.7% by mass to 6.6% by mass, from 3.7% by mass to 6.4% by mass, from 3.7% by mass to 6.2% by mass, or from 3.7% by mass to 6.0% by mass (in particular, the boron content can be at least 3.2% by mass, from 3.2% by mass to 6.0% by mass, or from 3.5% by mass to 6.8% by mass).

The mass ratio of borate-to-carbonate of the boron-containing detergents of the present invention permits comparison of the properties of overbased detergents prepared using different starting materials and synthetic processes. Numerous metal borate salts can be formed depending on the boron source used and reaction conditions. For example, as is known in the art, the term 'calcium borate' encompasses compounds such as calcium metaborate ($CaB_2O_4$), colemanite ($CaB_3O_4(OH)_3 \cdot H_2O$), calcium tetraborate ($CaB_4O_7$) and mixtures thereof. As the equivalents of boron-to-calcium varies between these forms, a practical way to characterize the content of these salts in detergent compositions is to quantify their relative contribution to the total base number (TBN). Those skilled in the art may routinely deduce the total base number (TBN) of a detergent, the contribution of basic soaps to this TBN, and the contribution of metal carbonate to TBN using conventional titration methods. The basic borate salt content thus can easily be deduced as: borate salt (mgKOH/g)=Total Base Number (mgKOH/g)−basic soap content (mgKOH/g)−metal carbonate (mgKOH/g). From this, the mass ratio of borate:carbonate is simply the ratio of the borate salt content to the carbonate salt content.

Titration methods to deduce the borate:carbonate ratio are familiar to those skilled in the art. For example, digestion of a known quantity of an overbased detergent with an excess of perchloric acid followed by titration with potassium hydroxide would be expected to yield one or two inflection points. Such a process is known as back-titration. The volume of potassium hydroxide needed to reach the first inflection point equates to the base contribution of the sample, which can be used to calculate a total TBN value. The soap used to form the overbased detergent also contributes to the total base number of the sample so the second inflection point informs on the presence of acids in the mixture following digestion of basic soaps with perchloric acid. This value can be used to the contribution made by the basic soaps to the total TBN of the detergent. Finally, the metal carbonate content is commonly determined by digesting a known quantity of the overbased detergent in acid to liberate carbon dioxide. The liberated gas is captured in solution. The carbonated solution can then be titrated to determine the amount of $CO_2$ liberated and thus the metal carbonate content of the detergent sample. By such methods, values for the total base number (TBN) of the detergent sample, the basic soap content, and the metal carbonate content can be determined. As set out above, simple arithmetic gives the borate salt content and so enables a calculation of the mass ratio of borate-to-carbonate. An illustration of how these determinations may be made is provided hereinbelow in relation to Example A4.

Mass ratio of borate to carbonate (typically calculated as salts). Boron-containing overbased salicylate detergents according to the present invention can have a mass ratio of borate to carbonate from 0.75 to 6.0, from 0.75 to 5.5, from 0.75 to 5.0, from 0.75 to 4.5, from 0.75 to 4.0, from 0.75 to 3.5, from 0.75 to 3.0, from 1.0 to 6.0, from 1.0 to 5.5, from 1.0 to 5.0, from 1.0 to 4.5, from 1.0 to 4.0, from 1.0 to 3.5, from 1.0 to 3.0, from 1.3 to 6.0, from 1.3 to 5.5, from 1.3 to 5.0, from 1.3 to 4.5, from 1.3 to 4.0, from 1.3 to 3.5, from 1.3 to 3.0, from 1.6 to 6.0, from 1.6 to 5.5, from 1.6 to 5.0, from 1.6 to 4.5, from 1.6 to 4.0, from 1.6 to 3.5, or from 1.6 to 3.0 (in particular, the mass ratio of borate to carbonate can be from 0.75 to 6.0, from 1.0 to 5.0, or from 1.6 to 3.0).

Alkaline earth metals. Boron-containing overbased salicylate detergents according to the present invention can comprise calcium and/or magnesium as alkaline earth metal(s). Boron-containing overbased salicylate detergents according to the present invention can have an alkaline earth metal content, according to ASTM D4951, of at least 6.0% by mass, at least 6.5% by mass, at least 7.0% by mass, at least 7.5% by mass, or at least 8.0% by mass, and/or an alkaline earth metal content of at most 13% by mass, at most 12.7% by mass, at most 12.4% by mass, at most 12.1% by mass, at most 11.8% by mass, or at most 11.5% by mass. Thus, the alkaline earth metal (e.g., combined calcium and magnesium) content can be from 6.0% by mass to 13% by mass, from 6.0% by mass to 12.7% by mass, from 6.0% by mass to 12.4% by mass, from 6.0% by mass to 12.1% by mass, from 6.0% by mass to 11.8% by mass, from 6.0% by mass to 11.5% by mass, from 6.5% by mass to 13% by mass, from 6.5% by mass to 12.7% by mass, from 6.5% by mass to 12.4% by mass, from 6.5% by mass to 12.1% by mass, from 6.5% by mass to 11.8% by mass, from 6.5% by mass to 11.5% by mass, from 7.0% by mass to 13% by mass, from 7.0% by mass to 12.7% by mass, from 7.0% by mass to 12.4% by mass, from 7.0% by mass to 12.1% by mass, from 7.0% by mass to 11.8% by mass, from 7.0% by mass to 11.5% by mass, from 7.5% by mass to 13% by mass, from 7.5% by mass to 12.7% by mass, from 7.5% by mass to 12.4% by mass, from 7.5% by mass to 12.1% by mass, from 7.5% by mass to 11.8% by mass, from 7.5% by mass to 11.5% by mass, from 8.0% by mass to 13% by mass, from 8.0% by mass to 12.7% by mass, from 8.0% by mass to 12.4% by mass, from 8.0% by mass to 12.1% by mass, from 8.0% by mass to 11.8% by mass, or from 8.0% by mass to 11.5% by mass (in particular, the alkaline earth metal content and/or the combined calcium and magnesium content can be at least 7.0% by mass, from 7.0% by mass to 12.5% by mass, or from 6.5% by mass to 11.8% by mass).

Hydrocarbyl substitution. In particular, boron-containing overbased salicylate detergents according to the present invention can have a hydrocarbyl substitution comprising 9 to 30 carbon atoms, comprising a $C_{14}$ to $C_{24}$ alkyl or alkenyl moiety, or comprising a $C_{14}$ to $C_{19}$ alkyl or alkenyl moiety.

Alkaline earth metal to boron mass ratio. Boron-containing overbased salicylate detergents according to the present invention can have a mass ratio of alkaline earth metal to boron from 1.3 to 5.8, from 1.3 to 5.5, from 1.3 to 5.2, from 1.3 to 4.9, from 1.3 to 4.7, from 1.3 to 4.5, from 1.3 to 4.2, from 1.3 to 3.9, from 1.3 to 3.6, from 1.3 to 3.3, from 1.5 to 5.8, from 1.5 to 5.5, from 1.5 to 5.2, from 1.5 to 4.9, from 1.5 to 4.7, from 1.5 to 4.5, from 1.5 to 4.2, from 1.5 to 3.9, from 1.5 to 3.6, from 1.5 to 3.3, from 1.6 to 5.8, from 1.6 to 5.5, from 1.6 to 5.2, from 1.6 to 4.9, from 1.6 to 4.7, from 1.6 to 4.5, from 1.6 to 4.2, from 1.6 to 3.9, from 1.6 to 3.6, from 1.6 to 3.3, from 1.7 to 5.8, from 1.7 to 5.5, from 1.7 to 5.2, from 1.7 to 4.9, from 1.7 to 4.7, from 1.7 to 4.5, from 1.7 to 4.2, from 1.7 to 3.9, from 1.7 to 3.6, or from 1.7 to 3.3 (in particular, from 1.3 to 5.8, from 1.5 to 5.5, from 1.7 to 4.5, or from 1.6 to 3.6).

Although the compositions and methods described herein involve overbased alkaline earth metal hydrocarbyl-substituted salicylate detergents, with a variety of specifications on various parameters, boration can be accomplished on any detergent, whether overbased, neutral, underbased, or sans alkaline earth metal, using any valent ion, such as based on alkali metals, Group 13 metals, or even ashless ions (such as ammonium ions, etc.), as well as on any detergent category, such as sulfonates, phenates, or carboxylates.

Neutral detergents generally are those that contain stoichiometrically equivalent amounts of the (alkaline earth metal) ion component in relation to the amount of (Lewis) acidic moieties present in the detergent. Underbased detergents generally are those that contain stoichiometrically lower amounts of the (alkaline earth metal) ion component in relation to the amount of (Lewis) acidic moieties present in the detergent. Thus, in general, neutral and underbased detergents can typically have a relatively low basicity, when compared to their overbased counterparts. The term "overbased," for example in connection with detergents, is used to designate the fact that the (alkaline earth metal) ion component is present in stoichiometrically larger amounts than the corresponding (Lewis) acid component.

In particular, boron-containing overbased salicylate detergents according to the present invention may be present in various lubricating oil compositions in amounts that may depend upon the lubricant application, e.g., from 0.03 to 6.0% by mass, from 0.05 to 0.7% by mass, from 0.07 to 2.0% by mass, or from 0.10 to 4.0% by mass, based on the total mass of the composition. Additionally, or alternatively, the boron-containing overbased salicylate detergent may be present in lubricating oil compositions in an amount sufficient to provide the composition with from 30 to 2000 parts per million by mass (ppm) of calcium, based on the mass of the composition, in particular, from 45 to 750 ppm, from 100 to 1400 ppm, or from 500 to 1800 ppm. Further, additionally or alternatively, the boron-containing overbased salicylate detergent may be present in lubricating oil compositions in an amount sufficient to provide the composition with from 20 to 500 ppm, based on the mass of the composition, in particular from 30 to 200 ppm, from 60 to 350 ppm, or from 100 to 450 ppm. Boron and/or calcium content can be measured in accordance with ASTM D4951.

Non-Calcium-Salicylate Detergents

In some embodiments, the additive package and/or the lubricating oil composition may further comprise a detergent other than one or more of the boron-containing overbased alkaline earth metal salicylates according to the present disclosure. In other embodiments, the additive package and/or the lubricating oil composition may further comprise substantially no other detergents, aside from the boron-containing overbased alkaline earth metal salicylate according to the present disclosure.

When the lubricating oil composition comprises an additional detergent, it may be an unborated alkaline earth metal detergent, such as an unborated but overbased alkaline earth metal detergent. These detergents are typically sufficiently oil-soluble or dispersible such as to remain dissolved or dispersed in an oil in order to be transported by the oil to their intended site of action. Additional unborated detergents are known in the art and may include neutral and overbased alkaline earth metal (e.g., calcium and/or magnesium) salts with acidic substances such as sulfonic acids, carboxylic acids, alkyl phenols, sulfurized alkyl phenols, and mixtures thereof. Additionally, or alternatively, when present, the additional unborated detergent can comprise or be a neutral or overbased unborated alkaline earth metal salicylate.

Examples of additional unborated detergents useful in tandem with the boron-containing overbased alkaline earth metal salicylate in the lubricant additive package concentrates and/or lubricating oil compositions of the present disclosure may include, but are not necessarily limited to, neutral and/or overbased salts of such substances as alkaline earth metal phenates; sulfurized alkaline earth metal phenates (e.g., wherein each aromatic group has one or more aliphatic groups to impart hydrocarbon solubility); alkaline earth metal sulfonates (e.g., wherein each sulfonic acid moiety is attached to an aromatic nucleus, which in turn usually contains one or more aliphatic substituents to impart hydrocarbon solubility); alkaline earth metal salts of hydrolyzed phosphosulfurized olefins (e.g., having 10 to 2000 carbon atoms) and/or of hydrolyzed phosphosulfurized alcohols and/or aliphatic-substituted phenolic compounds (e.g., having 10 to 2000 carbon atoms); alkaline earth metal salts of aliphatic carboxylic acids and/or aliphatic substituted cycloaliphatic carboxylic acids; unborated alkaline earth metal hydrocarbyl-substituted salicylates (e.g., having 10 to 1000 carbon atoms); and combinations and/or reaction products thereof; as well as many other similar alkaline earth metal salts of oil-soluble organic acids. Mixtures of neutral and/or overbased salts of two or more different non-salicylic acids can be used, if desired (e.g., one or more overbased calcium phenates with one or more overbased calcium sulfonates). Optionally, a boron-containing neutral or overbased non-salicylate detergent may be present in the additive package and/or the lubricating oil composition, instead of or in addition to any additional unborated detergent.

Methods for the production of oil-soluble neutral and overbased unborated alkaline earth metal detergents are well known to those skilled in the art and are extensively reported in the patent literature.

When present, the combination of the boron-containing alkaline earth metal salicylate, plus the additional detergent may collectively provide the lubricating oil composition with from 30 to 2000 parts per million by mass (ppm) of calcium, based on the mass of the composition, in particular, from 45 to 750 ppm, from 100 to 1400 ppm, or from 500 to 1800 ppm. Further, additionally or alternatively, the boron-containing overbased salicylate detergent may be present in lubricating oil compositions in an amount sufficient to provide the composition with from 20 to 500 ppm, based on the mass of the composition, in particular from 30 to 200 ppm, from 60 to 350 ppm, or from 100 to 450 ppm. Boron and/or calcium content can be measured in accordance with ASTM D5185.

Lubricating Oil Basestock/Diluent

The lubricating oil basestock/diluent in boron-containing detergent components, boron-containing detergent-containing lubricant additive package concentrates, and/or boron-containing detergent-containing lubricant oil compositions may be any suitable lubricating oil basestock known in the art. Both natural and synthetic lubricating oil basestocks may be suitable. Natural lubricating oils may include animal oils, vegetable oils (e.g., castor oil and lard oil), petroleum oils, mineral oils, oils derived from coal or shale, and combinations thereof. One particular natural lubricating oil includes or is mineral oil.

Suitable mineral oils may include all common mineral oil basestocks, including oils that are naphthenic or paraffinic in chemical structure. Suitable oils may be refined by conventional methodology using acid, alkali, and clay, or other agents such as aluminum chloride, or they may be extracted oils produced, for example, by solvent extraction with solvents such as phenol, sulfur dioxide, furfural, dichlorodiethyl ether, etc., or combinations thereof. They may be hydrotreated or hydrofined, dewaxed by chilling or catalytic dewaxing processes, hydrocracked, or some combination thereof. Suitable mineral oils may be produced from natural crude sources or may be composed of isomerized wax materials, or residues of other refining processes.

Synthetic lubricating oil basestocks may include hydrocarbon oils and halo-substituted hydrocarbon oils such as oligomerized, polymerized, and interpolymerized olefins (e.g., polybutylenes, polypropylenes, propylene, isobutylene copolymers, chlorinated polylactenes, poly(1-hexenes), poly (1-octenes), poly-(1-decenes), etc., and mixtures thereof); alkylbenzenes (e.g., dodecyl-benzenes, tetradecylbenzenes, dinonyl-benzenes, di(2-ethylhexyl)benzene, etc.); polyphenyls (e.g., biphenyl s, terphenyls, alkylated polyphenyls, etc.); alkylated diphenyl ethers, alkylated diphenyl sulfides, as well as their derivatives, analogs, and homologs thereof, and the like; and combinations and/or reaction products thereof.

In some embodiments, oils from this class of synthetic oil basestocks may comprise or be polyalphaolefins (PAO), including hydrogenated oligomers of an alpha-olefin, particularly oligomers of 1-decene, such as those produced by free radical processes, Ziegler catalysis, or cationic catalysis. They may, for example, be oligomers of branched or straight chain alpha-olefins having from 2 to 16 carbon atoms, specific non-limiting examples including polypropenes, polyisobutenes, poly-1-butenes, poly-1-hexenes, poly-1-octenes, poly-1-decene, poly-1-dodecene, and mixtures and/or interpolymers/copolymers thereof.

Synthetic lubricating oil basestocks may additionally or alternatively include alkylene oxide polymers, interpolymers, copolymers, and derivatives thereof, in which any (most) terminal hydroxyl groups have been modified by esterification, etherification, etc. This class of synthetic oils may be exemplified by: polyoxyalkylene polymers prepared by polymerization of ethylene oxide or propylene oxide; the alkyl and aryl ethers of these polyoxyalkylene polymers (e.g., methyl-polyisopropylene glycol ether having an average Mn of ~1000 Daltons, diphenyl ether of polypropylene glycol having an average Mn from about 1000 to about 1500 Daltons); and mono- and poly-carboxylic esters thereof (e.g., acetic acid ester(s), mixed $C_3$-$C_8$ fatty acid esters, $C_{12}$ oxo acid diester(s) of tetraethylene glycol, or the like, or combinations thereof).

Another suitable class of synthetic lubricating oil basestocks may comprise the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoethers, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, a complex ester formed by reacting one mole of sebacic acid with two moles of tetraethylene glycol and two moles of 2-ethyl-hexanoic acid, and the like, and combinations thereof. A preferred type of oil from this class of synthetic oils may include adipates of $C_4$ to $C_{12}$ alcohols.

Esters useful as synthetic lubricating oil basestocks may additionally or alternatively include those made from $C_5$-$C_{12}$ monocarboxylic acids, polyols, and/or polyol ethers, e.g., such as neopentyl glycol, trimethylolpropane pentaerythritol, dipentaerythritol, tripentaerythritol, and the like, as well as combinations thereof.

The lubricating oil basestocks may be derived from unrefined oils, refined oils, re-refined oils, or mixtures thereof. Unrefined oils are obtained directly from a natural source or synthetic source (e.g., coal, shale, or tar sands bitumen) without further purification or treatment. Examples of unrefined oils may include a shale oil obtained directly from a retorting operation, a petroleum oil obtained directly from distillation, or an ester oil obtained directly from an esterification process, each or a combination of which may then be used without further treatment. Refined oils are similar to the unrefined oils, except that refined oils have typically been treated in one or more purification steps to change chemical structure and/or to improve one or more properties. Suitable purification techniques may include distillation, hydrotreating, dewaxing, solvent extraction, acid or base extraction, filtration, and percolation, all of which are known to those skilled in the art. Re-refined oils may be obtained by treating used and/or refined oils in processes similar to those used to obtain refined oils in the first place. Such re-refined oils may be known as reclaimed or reprocessed oils and may often additionally be processed by techniques for removal of spent additives and oil breakdown products.

Another additional or alternative class of suitable lubricating oil basestocks may include those basestocks produced from oligomerization of natural gas feed stocks or isomerization of waxes. These basestocks can be referred to in any number of ways but commonly they are known as Gas-to-Liquid (GTL) or Fischer-Tropsch basestocks.

The lubricating oil basestock according to the present disclosure may be a blend of one or more of the oils/basestocks described herein, whether of a similar or different type, and a blend of natural and synthetic lubricating oils (i.e., partially synthetic) is expressly contemplated for this disclosure.

Lubricating oils can be classified as set out in the American Petroleum Institute (API) publication "Engine Oil Licensing and Certification System", Industry Services Department, Fourteenth Edition, December 1996, Addendum 1, December 1998, in which oils are categorized as follows:

a) Group I basestocks contain less than 90 percent saturates and/or greater than 0.03 percent sulfur and have a viscosity index greater than or equal to 80 and less than 120;

b) Group II basestocks contain greater than or equal to 90 percent saturates and less than or equal to 0.03 percent sulfur and have a viscosity index greater than or equal to 80 and less than 120;

c) Group III basestocks contain greater than or equal to 90 percent saturates and less than or equal to 0.03 percent sulfur and have a viscosity index greater than or equal to 120;

d) Group IV basestocks are polyalphaolefins (PAO); and, e) Group V basestocks include all other basestock oils not included in Groups I, II, III, or IV.

In an embodiment of the present disclosure, the lubricating oil basestock may comprise or be a mineral oil or a mixture of mineral oils, in particular mineral oils of Group II and/or Group III (of the API classification). Additionally, or alternatively, the lubricating oil basestock may comprise or be a synthetic oil such as a Fischer Tropsch/GTL-derived oil of any Group, a polyalphaolefin (Group IV), and/or an oil of Group V. In embodiments where desired formulation viscosities are very low (e.g., less than 4.0 cSt or less than 3.5 cSt), it may be advantageous for the lubricating oil basestock to be a Group IV (polyalphaolefin) basestock or mixture of Group IV basestocks, or to be comprised of at least 40% (e.g., at least 50%, at least 60%, at least 70%, at least 80%, or at least 90%) by mass of one or more Group IV basestocks.

In some embodiments, the lubricating oil basestock(s), individually or collectively, may exhibit a kinematic viscosity at 100° C. (KV100), as measured by ASTM D445, of from 1.0 cSt to 40 cSt (e.g., from 1.0 cSt to 30 cSt, from 1.0 cSt to 20 cSt, from 1.0 cSt to 15 cSt, from 1.0 cSt to 10 cSt, from 1.0 cSt to 8.5 cSt, from 1.0 cSt to 7.5 cSt, from 1.0 cSt to 6.5 cSt, from 1.0 cSt to 5.5 cSt, from 1.0 cSt to 5.0 cSt, from 1.0 cSt to 4.5 cSt, from 1.0 cSt to 4.0 cSt, from 1.0 cSt to 3.5 cSt, from 1.0 cSt to 3.0 cSt, from 1.0 cSt to 2.5 cSt, from 1.0 cSt to 2.0 cSt, from 1.5 cSt to 30 cSt, from 1.5 cSt to 20 cSt, from 1.5 cSt to 15 cSt, from 1.5 cSt to 10 cSt, from 1.5 cSt to 8.5 cSt, from 1.5 cSt to 7.5 cSt, from 1.5 cSt to 6.5 cSt, from 1.5 cSt to 5.5 cSt, from 1.5 cSt to 5.0 cSt, from 1.5 cSt to 4.5 cSt, from 1.5 cSt to 4.0 cSt, from 1.5 cSt to 3.5 cSt, from 1.5 cSt to 3.0 cSt, from 1.5 cSt to 2.5 cSt, from 2.0 cSt to 30 cSt, from 2.0 cSt to 20 cSt, from 2.0 cSt to 15 cSt, from 2.0 cSt to 10 cSt, from 2.0 cSt to 8.5 cSt, from 2.0 cSt to 7.5 cSt, from 2.0 cSt to 6.5 cSt, from 2.0 cSt to 5.5 cSt, from 2.0 cSt to 5.0 cSt, from 2.0 cSt to 4.5 cSt, from 2.0 cSt to 4.0 cSt, from 2.0 cSt to 3.5 cSt, from 2.0 cSt to 3.0 cSt, from 2.5 cSt to 30 cSt, from 2.5 cSt to 20 cSt, from 2.5 cSt to 15 cSt, from 2.5 cSt to 10 cSt, from 2.5 cSt to 8.5 cSt, from 2.5 cSt to 7.5 cSt, from 2.5 cSt to 6.5 cSt, from 2.5 cSt to 5.5 cSt, from 2.5 cSt to 5.0 cSt, from 2.5 cSt to 4.5 cSt, from 2.5 cSt to 4.0 cSt, from 2.5 cSt to 3.5 cSt, from 3.0 cSt to 30 cSt, from 3.0 cSt to 20 cSt, from 3.0 cSt to 15 cSt, from 3.0 cSt to 10 cSt, from 3.0 cSt to 8.5 cSt, from 3.0 cSt to 7.5 cSt, from 3.0 cSt to 6.5 cSt, from 3.0 cSt to 5.5 cSt, from 3.0 cSt to 5.0 cSt, from 3.0 cSt to 4.5 cSt, from 3.0 cSt to 4.0 cSt, from 4.0 cSt to 30 cSt, from 4.0 cSt to 20 cSt, from 4.0 cSt to 15 cSt, from 4.0 cSt to 10 cSt, from 4.0 cSt to 8.5 cSt, from 4.0 cSt to 7.5 cSt, from 4.0 cSt to 6.5 cSt, from 4.0 cSt to 5.5 cSt, or from 4 cSt to 5.0 cSt), in particular from 1.5 cSt to 40 cSt, from 2.0 cSt to 20 cSt, from 2.5 cSt to 10 cSt, or from 4.0 cSt to 40 cSt.

Non-Detergent Co-Additives

Co-additives commonly found in lubricants may, optionally, be included in the additive packages and/or the lubricating oil compositions according to the present disclosure. Suitable co-additives will be known to those skilled in the art. Some examples are described herein.

Ashless Dispersants

In some embodiments, the additive package concentrate and/or the lubricating oil composition may further comprise one or more basic nitrogen-containing ashless dispersants. Indeed, such nitrogen-containing ashless dispersant(s), when present, may advantageously be of structure (I):

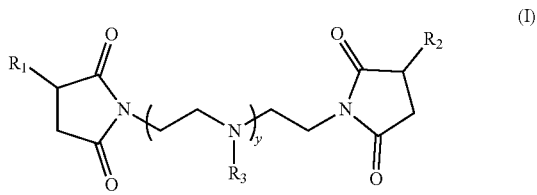

wherein: $R_1$ and $R_2$ are each independently a hydrocarbyl group (e.g., a polyisobutenyl moiety having a number average molecular weight (Mn) in particular from 500 to 5000 Daltons or from 750 to 2500 Daltons, as determined by GPC with reference to linear polystyrene standards, and/or a hydrocarbon group made by the metallocene-catalyzed polymerization of an α-olefin feedstock comprising 1-butene, 1-pentene, 1-hexene, 1-heptene, 1-octene, 1-nonene, 1-decene, 1-undecene, 1-dodecene, 1-tetradecene, 1-octadecene, or mixtures thereof, in particular consisting essentially of 1-octene, 1-decene, 1-dodecene, and mixtures thereof, a.k.a. metallocene-catalyzed poly(alpha-olefins), or mPAOs, having an Mn from 300 to 20000 Daltons, as determined by GPC with reference to linear polystyrene standards, e.g., from 400 to 15000 Daltons, from 450 to 10000 Daltons, from 500 to 8000 Daltons, from 650 to 6500 Daltons, from 800 to 5000 Daltons, or from 900 to 3000 Daltons; in particular from 300 to 20000 Daltons, from 500 to 8000 Daltons, or from 800 to 5000 Daltons); each $R_3$ is independently hydrogen, an acetyl moiety, or a moiety formed by reaction between ethylene carbonate and >N—$R_3$ (in particular, hydrogen or an acetyl moiety); and y is from 1 to 10 (in particular, from 3 to 10) and is the same for all molecules of structure (I) or is an average of all molecules of structure (I) in a mixture of molecules of structure (I).

Examples of such ashless dispersants may include polyisobutenyl succinimides, mPAO-based succinimides, polyisobutenyl succinamides, mPAO-based succinamides, mixed ester/amides of polyisobutenyl-substituted succinic acid, mixed ester/amides of mPAO-substituted succinic acid (mPAOSA), hydroxyesters of polyisobutenyl-substituted succinic acid, hydroxyesters of mPAO-substituted succinic acid, and Mannich condensation products of hydrocarbyl-substituted phenols, formaldehyde, and polyamines, as well as reaction products and mixtures thereof.

Such basic nitrogen-containing ashless dispersants may be used as lubricating oil additives and methods for their preparation are extensively described in the patent literature. Exemplary ashless dispersants of structure (I) may include the polyisobutenyl and/or mPAO succinimides and succinamides in which the polyisobutenyl and/or mPAO substituent(s) is(are) a long hydrocarbonaceous chain of greater than 36 carbons, e.g., greater than 40 carbon atoms. These PIB-based materials can be readily made by reacting a polyisobutenyl-substituted dicarboxylic acid material with a molecule-containing amine functionality. These mPAO-based materials can be readily made by reacting an mPAO functionalized with a dicarboxylic acid or an mPAO functionalized with an anhydride (such as reacted maleic acid) with a molecule-containing amine functionality. Examples of suitable amines, in either or both cases, may include polyamines such as polyalkylene polyamines, hydroxy-substituted polyamines, polyoxyalkylene polyamines, and combinations thereof. The amine functionality may be provided by polyalkylene polyamines such as tetraethylene pentamine and pentaethylene hexamine. Mixtures where the average number of nitrogen atoms per polyamine molecule is greater than 7 are also available. These are commonly called heavy polyamines or H-PAMs and may be commercially available under trade names such as HPA™ and HPA-X™ from DowChemical, E100™ from Huntsman Chemical, et al. Examples of hydroxy-substituted polyamines may include N-hydroxyalkyl-alkylene polyamines such as N-(2-hydroxyethyl)ethylene diamine, N-(2-hydroxyethyl)piperazine, and/or N-hydroxyalkylated alkylene diamines of the type described, for example, in U.S. Pat. No. 4,873,009. Examples of polyoxyalkylene polyamines may include polyoxyethylene and polyoxypropylene diamines and triamines having an average Mn from about 200 to about 2500 Daltons. Products of this type may be commercially available under the tradename Jeffamine™.

As is known in the art, reaction of the amine with the polyisobutenyl-substituted and/or mPAO-functionalized dicarboxylic acid material (suitably an alkenyl succinic anhydride or maleic anhydride) can be conveniently achieved by heating the reactants together, e.g., in an oil solution. Reaction temperatures of ~100° C. to ~250° C. and reaction times from ~1 to ~10 hours may be typical. Reaction ratios can vary considerably, but generally from about 0.1 to about 1.0 equivalents of dicarboxylic acid unit content may be used per reactive equivalent of the amine-containing reactant.

In particular, the ashless dispersant, when present, may include a polyisobutenyl succinimide formed from polyisobutenyl succinic anhydride and a polyalkylene polyamine such as tetraethylene pentamine or H-PAM, a mPAO-based succinimide formed from succinic anhydride-functionalized mPAO and a polyalkylene polyamine such as tetraethylene pentamine or H-PAM, or a combination or reaction product thereof. These dispersants, similarly to other dispersants known in the art, may be further treated (e.g., with a secondary nitrogen-capping agent such as acetic anhydride and/or ethylene carbonate, with a borating/boronating agent, and/or with an inorganic acid of phosphorus). Suitable examples may be found, for instance, in U.S. Pat. Nos. 3,254,025, 3,502,677, and 4,857,214.

When used, an ashless dispersant according to structure (I) may be present in an amount of from 0.1 to 30% by mass, based on the total mass of the additive package concentrate and/or lubricating oil composition, e.g., from 0.5 to 25% by mass or from 1.0 to 20% by mass.

Although borating of dispersants is known and may be desirable, in particular embodiments the dispersant(s) of structure (I) individually(collectively), and indeed all components of the additive package concentrates and/or lubricating oil compositions according to the present disclosure (altogether), may comprise from 20 to 500 ppm, based on the mass of the composition, in particular from 30 to 200 ppm, from 60 to 350 ppm, or from 100 to 450 ppm. Boron content can be measured in accordance with ASTM D5185

Antioxidants

Antioxidants are sometimes referred to as oxidation inhibitors and may increase the resistance (or decrease the susceptibility) of the lubricating oil composition to oxidation. They may work by combining with and modifying oxidative agents, such as peroxides and other free radical-forming compounds, to render them harmless, e.g., by decomposing them or by rendering inert a catalyst or facilitator of oxidation. Oxidative deterioration can be evidenced by sludge in the fluid with increased use, by varnish-like deposits on metal surfaces, and sometimes by viscosity increase.

A wide variety of oxidation inhibitors that are useful in lubricating oil compositions. See *Lubricants and Related Products*, Klamann, Wiley VCH, 1984; U.S. Pat. Nos. 4,798,684; and 5,084,197, for example.

Examples of suitable antioxidants may include, but are not limited to, copper-containing antioxidants, sulfur-containing antioxidants, aromatic amine-containing and/or amide-containing antioxidants, (hindered) phenolic antioxidants, dithiophosphates and derivatives, and the like, as well as combinations and certain reaction products thereof. Some antioxidants may be ashless (i.e., may contain few, if any, metal atoms other than trace or contaminants). In preferred embodiments, one or more antioxidants can be present in additive package concentrates and/or lubricating oil compositions according to the present disclosure. In particular, a lubricating oil composition of the present disclosure may comprise an aminic antioxidant, a (hindered) phenolic antioxidant, or a combination thereof.

Phenolic antioxidants may be ashless (metal-free) phenolic compounds or neutral or basic metal salts of certain phenolic compounds. Typical phenolic antioxidants are hindered phenolics which contain a sterically hindered hydroxyl group, and these include those derivatives of dihydroxy aryl compounds in which the hydroxyl groups are in the o- or p-position to each other. Typical phenolic antioxidants can include hindered phenols substituted with $C_{6+}$ alkyl groups and the alkylene coupled derivatives of these hindered phenols. Examples of phenolic materials of this type may include, but are not necessarily limited to, 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; 2-methyl-6-t-butyl-4-dodecyl phenol, and combinations thereof. Other useful hindered mono-phenolic antioxidants may include, for example, hindered 2,6-di-alkyl-phenolic propionic ester derivatives. Bis-phenolic antioxidants may also be used. Examples of ortho-coupled phenols may include 2,2'-bis(4-heptyl-6-t-butyl-phenol); 2,2'-bis(4-octyl-6-t-butyl-phenol); 2,2'-bis(4-dodecyl-6-t-butyl-phenol); and combinations thereof. Para-coupled bisphenols may include, for example, 4,4'-bis(2,6-di-t-butyl phenol) and/or 4,4'-methylene-bis(2,6-di-t-butyl phenol).

Effective amounts of one or more catalytic antioxidants may additionally or alternatively be used. Catalytic antioxidants can comprise a) one or more oil soluble polymetal organic compounds; and b) one or more substituted N,N'-diaryl-o-phenylenediamine compounds, or c) one or more hindered phenol compounds, or a combination of both b) and c). Catalytic antioxidants are disclosed in U.S. Pat. No. 8,048,833.

Non-phenolic oxidation inhibitors may include (aromatic) aminic antioxidants, used as such or in combination with phenolics. Typical examples of non-phenolic antioxidants can include, but are not necessarily limited to, alkylated and non-alkylated aromatic amines such as aromatic monoamines of the formula $R^4R^5R^6N$, where $R^4$ is an aliphatic, aromatic, or substituted aromatic group, $R^5$ is an aromatic or a substituted aromatic group, and $R^6$ is H, alkyl, aryl or $R^7S(O)_xR^8$, where $R^7$ is an alkylene, alkenylene, or aralkylene group, $R^8$ is an alkyl group, or an alkenyl, aryl, or alkaryl group, and x is 0, 1, or 2. The aliphatic group $R^4$ may contain 1 to 20 carbon atoms (e.g., 6 to 12 carbon atoms). The aliphatic group can typically be a saturated aliphatic group. In embodiments, both $R^4$ and $R^5$ are aromatic or substituted aromatic groups, and the aromatic group may be a fused ring aromatic group such as naphthyl. Aromatic groups $R^4$ and $R^5$ may be joined together with other groups such as S.

Typical aromatic aminic antioxidants can have alkyl substituent groups of at least about 6 carbon atoms. Examples of aliphatic groups can include hexyl, heptyl, octyl, nonyl, decyl, and combinations, inter alia. Generally, the aliphatic groups can contain no more than about 14 carbon atoms. The general types of aminic antioxidants useful as lubricant additives can include diphenylamines, phenyl naphthylamines, phenothiazines, imidodibenzyls, diphenyl phenylene diamines, and the like, as well as combinations thereof. Mixtures of two or more amines may also be useful. Polymeric aminic antioxidants can also be useful. Examples of aromatic aminic antioxidants can include p,p'-dioctyldiphenylamine; t-octylphenyl-alpha-naphthylamine; phenyl-alpha-naphthylamine; p-octylphenyl-alpha-naphthylamine; bis(nonylphenyl)amines; N-phenyl-benzeneamide; and the like; and combinations thereof.

Sulfur-containing antioxidants can be oil-soluble and/or oil-dispersible and may include, but are not necessarily limited to, sulfurized alkyl phenols and/or alkali/alkaline earth metal salts thereof. Non-limiting examples can include sulfurized $C_4$ to $C_{25}$ olefin(s), sulfurized aliphatic ($C_7$-$C_{29}$) hydrocarbyl fatty acid ester(s), ashless sulfurized phenolic antioxidant(s), sulfur-containing organo-molybdenum compound(s), and combinations thereof. For further information, on sulfurized materials useful as antioxidants, please see U.S. Pat. No. 10,731,101 (e.g., columns 15-22).

In particular, when present, antioxidants can include a hindered phenol and/or an optionally alkylated diarylamine. When present, one or more antioxidants may be used in a collective amount from 0.01 to 10 mass %, e.g., from 0.05 to 5 mass %, from 0.1 to 3 mass %, or from 0.5 to 10 mass %.

Corrosion Inhibitors

Corrosion inhibitors may be used to reduce the corrosion of metals and are often alternatively referred to as metal deactivators or metal passivators. Some corrosion inhibitors may alternatively be characterized as antioxidants.

Suitable corrosion inhibitors may include nitrogen and/or sulfur-containing heterocyclic compounds such as triazoles (e.g., benzotriazoles), substituted thiadiazoles, imidazoles, thiazoles, tetrazoles, hydroxyquinolines, oxazolines, imidazolines, thiophenes, indoles, indazoles, quinolines, benzoxazines, dithiols, oxazoles, oxatriazoles, pyridines, piperazines, triazines and derivatives of any one or more thereof. A particular corrosion inhibitor is a benzotriazole represented by the structure:

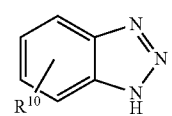

wherein $R^{10}$ is absent or is a $C_1$ to $C_{20}$ hydrocarbyl or substituted hydrocarbyl group which may be linear or branched, saturated or unsaturated. It may contain ring structures that are alkyl or aromatic in nature and/or contain heteroatoms such as N, O, or S. Examples of suitable compounds may include benzotriazole, alkyl-substituted benzotriazoles (e.g., tolyltriazole, ethylbenzotriazole, hexylbenzotriazole, octylbenzotriazole, etc.), aryl substituted benzotriazole, alkylaryl- or arylalkyl-substituted benzotriazoles, and the like, as well as combinations thereof. For instance, the triazole may comprise or be a benzotriazole and/or an alkylbenzotriazole in which the alkyl group contains from 1 to about 20 carbon atoms or from 1 to about 8 carbon atoms. In some embodiments, the corrosion inhibitor may comprise or be benzotriazole and/or tolyltriazole.

Additionally, or alternatively, the corrosion inhibitor may include substituted thiadiazole represented by the structure:

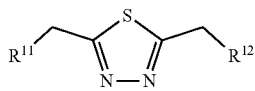

wherein $R^{11}$ and $R^{12}$ are independently hydrogen or a hydrocarbon group, which group may be aliphatic or aromatic, including cyclic, alicyclic, aralkyl, aryl, and alkaryl. These substituted thiadiazoles are derived from the 2,5-dimercapto-1,3,4-thiadiazole (DMTD) molecule. Many derivatives of DMTD have been described in the art, and any such compounds can be included in the lubricating oil composition used in the present disclosure. For example, U.S. Pat. Nos. 2,719,125; 2,719,126; and 3,087,937; describe the preparation of various 2,5-bis-(hydrocarbon dithio)-1,3,4-thiadiazoles.

Further, additionally or alternatively, the corrosion inhibitor may include one or more other derivatives of DMTD, such as a carboxylic ester in which $R^{11}$ and $R^{12}$ may be joined to the sulfide sulfur atom through a carbonyl group. Preparation of these thioester-containing DMTD derivatives is described, for example, in U.S. Pat. No. 2,760,933. DMTD derivatives produced by condensation of DMTD with alpha-halogenated aliphatic monocarboxylic carboxylic acids having at least 10 carbon atoms are described, for example, in U.S. Pat. No. 2,836,564. This process produces DMTD derivatives wherein $R^{11}$ and $R^{12}$ are HOOC—CH ($R^{13}$)—, with $R^{13}$ being a hydrocarbyl group). DMTD derivatives further produced by amidation or esterification of these terminal carboxylic acid groups may also be useful.

The preparation of 2-hydrocarbyldithio-5-mercapto-1,3,4-thiadiazoles is described, for example, in U.S. Pat. No. 3,663,561.

A particular class of DMTD derivatives may include mixtures of a 2-hydrocarbyldithio-5-mercapto-1,3,4-thiadiazole and a 2,5-bis-hydrocarbyldithio-1,3,4-thiadiazole. Such mixtures may be sold under the tradename HiTEC® 4313 and are commercially available from Afton Chemical.

In particular, when present, an additive package concentrate and/or lubricating oil composition according to the present disclosure may comprise a substituted thiadiazole, a substituted benzotriazole, or a combination thereof.

When desired, corrosion inhibitors can be used in any effective amount, but, when used, may typically be used in amounts from about 0.001 to 5.0 mass %, based on the mass of the concentrate/composition, e.g., from 0.01 to 3.0 mass % or from 0.03 to 1.0 mass %.

Friction Modifiers

Organic friction modifiers (OFMs; a.k.a. ashless FMs) may be present in the additive package concentrates and/or lubricating oil compositions according to the present disclosure and are known generally. For instance, OFMs may include esters formed by reacting carboxylic acids and/or anhydrides with alkanols and/or amine-based FMs. Other useful friction modifiers may generally include a polar terminal group (e.g., carboxyl or hydroxyl) covalently bonded to an oleophilic hydrocarbon chain. Esters of carboxylic acids and anhydrides with alkanols are described in U.S. Pat. No. 4,702,850. Examples of other conventional OFMs can be found in M. Belzer, Journal of Tribology (1992), Vol. 114, pp. 675-682, and M. Belzer and S. Jahanmir, Lubrication Science (1988), Vol. 1, pp. 3-26. Typically, the total amount of organic/ashless friction modifier in a lubricating oil composition according to the present disclosure does not exceed 5 mass %, based on the total mass of the composition, e.g., does not exceed 2 mass % or does not exceed 0.5 mass %; optionally, OFMs may also be present in at least 0.05 mass %, based on the total mass of the composition, e.g., at least 0.1 mass % or at least 0.2 mass %.

Illustrative friction modifiers that may be useful in the lubricating compositions described herein include, for example, alkoxylated fatty acid esters, alkanolamides, polyol fatty acid esters, borated glycerol fatty acid esters, fatty alcohol ethers, and combinations thereof.

Illustrative alkoxylated fatty acid esters may include, for example, polyoxyethylene stearate, fatty acid polyglycol ester, and the like. These can include polyoxypropylene stearate, polyoxybutylene stearate, polyoxyethylene isostearate, polyoxypropylene isostearate, polyoxyethylene palmitate, and the like, as well as combinations thereof.

Illustrative alkanolamides may include, for example, lauric acid diethylalkanolamide, palmic acid diethylalkanolamide, and the like. These can include oleic acid diethyalkanolamide, stearic acid diethylalkanolamide, oleic acid di ethylalkanolamide, polyethoxylated hydrocarbylamides, polypropoxylated hydrocarbylamides, and the like, as well as combinations thereof.

Illustrative polyol fatty acid esters may include, for example, glycerol monooleate, saturated mono-, di-, and tri-glyceride esters, glycerol monostearate, hydroxyl-containing polyol esters, and the like, as well as combinations thereof.

Illustrative borated glycerol fatty acid esters may include, for example, borated glycerol monooleate, borated saturated mono-, di-, and tri-glyceride esters, borated glycerol monostearate, and the like, as well as combinations thereof. Additionally, or alternatively to glycerol polyols, these can include trimethylolpropane, pentaerythritol, sorbitan, and the like. These esters can be polyol monocarboxylate esters, polyol dicarboxylate esters, and/or, on occasion, polyoltricarboxylate esters. In particular, OFMs can include glycerol monooleates, glycerol dioleates, glycerol trioleates, glycerol monostearates, glycerol distearates, and glycerol tristearates and the corresponding glycerol monopalmitates, glycerol dipalmitates, glycerol tripalmitates, the respective isostearates, linoleates, and the like, as well as combinations thereof. Ethoxylated, propoxylated, butoxylated fatty acid esters of polyols, especially using glycerol as underlying polyol, may be useful as OFMs.

Illustrative fatty alcohol ethers may include, for example, stearyl ether, myristyl ether, and the like, as well as combinations thereof. Alcohols, including those that have carbon numbers from $C_3$ to $C_{50}$, can be ethoxylated, propoxylated, or butoxylated to form the corresponding fatty alkyl ethers. The underlying alcohol portion may comprise or be stearyl, myristyl, palmityl, $C_{11}$-$C_{13}$ hydrocarbon, oleyl, isostearyl, and the like.

Other ashless friction modifiers may include derivatives of polyalkylene polyamines and/or ethoxylated long chain amines. The derivatives of polyalkylene polyamines may advantageously include succinimides of a defined structure or may be simple amides. The polyalkylene portion may advantageously have from 2 to 4 carbons.

Suitable succinimides derived from polyethylene polyamines may include those of the following structure:

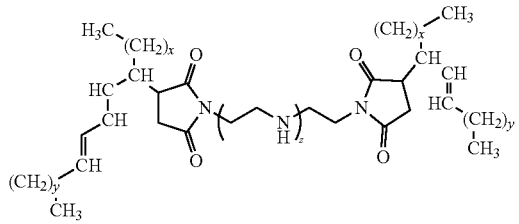

wherein x+y may be from 8 to 15 and z may be 0 or an integer from 1 to 5, in particular wherein x+y may be from 11 to 15 (e.g., 13) and z may be from 1 to 3. More broadly, such friction modifiers can be expressed using the following general structure:

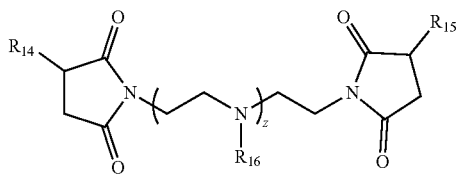

wherein each of $R_{14}$ and $R_{15}$ is independently:

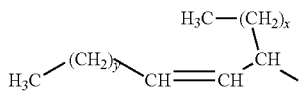

such that x+y is from 8 to 15 (in particular, from 11 to 15, e.g., 13) and z is 0 or an integer from 1 to 5 (in particular, an integer from 1 to 5 or an integer from 1 to 3); and wherein each $R_{16}$ is independently hydrogen, an acetyl moiety, or a moiety formed by reaction between ethylene carbonate and >N—$R_{16}$ (in particular, hydrogen or an acetyl moiety).

Preparation of such friction modifiers is described, for example, in U.S. Pat. No. 5,840,663.

The above succinimides may be post-reacted with acetic anhydride to form friction modifiers in which each $R_{16}$ is independently an acetyl group, as exemplified by the following structure (in which z=1):

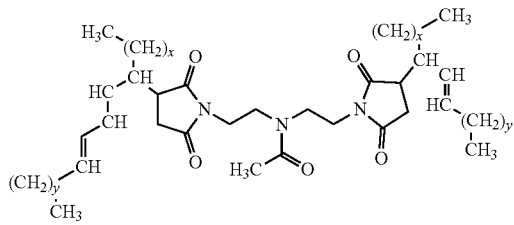

Preparation of this friction modifier, e.g., can be found in U.S. Patent Application Publication No. 2009/0005277. Post reaction with other reagents, e.g., borating agents, is also known in the art. When present, such succinimide friction modifiers may be used in any effective amount.

An example of an alternative simple amide friction modifier may have the following structure:

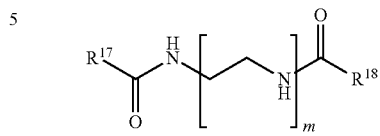

wherein $R^{17}$ and $R^{18}$ may be the same or different alkyl groups. For example, $R^{17}$ and $R^{18}$ may be $C_{14}$ to $C_{20}$ alkyl groups, which may be linear or branched, and m can be an integer from 1 to 5. In particular, $R^{17}$ and $R^{18}$ may both be derived from iso-stearic acid, and m may be 4. When present, such simple amides may be used in any effective amount.

Suitable ethoxylated amine friction modifiers may include or be reaction products of primary amines and/or diamines with ethylene oxide. The reaction with ethylene oxide may be suitably carried out using a stoichiometry such that substantially all primary and secondary amines may be converted to tertiary amines. Such amines may have the exemplary structures:

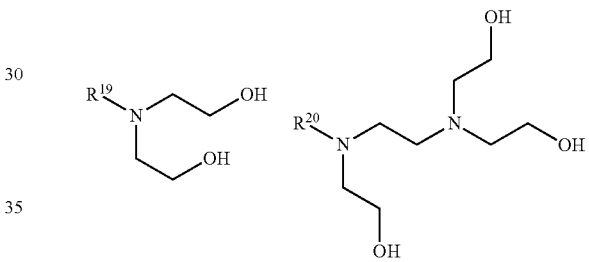

wherein $R^{19}$ and $R^{20}$ may be alkyl groups, or alkyl groups containing sulfur or oxygen linkages, containing from about 10 to 20 carbon atoms. Exemplary ethoxylated amine friction modifiers may include materials in which $R^{19}$ and/or $R^{20}$ may contain from 16 to 20 carbon atoms, e.g., from 16 to 18 carbon atoms. Materials of this type may be commercially available and sold under the tradenames of Ethomeen® and Ethoduomeen® by Akzo Nobel. Suitable materials from Akzo Nobel may include Ethomeen® T/12 and Ethoduomeen® T/13, inter alia. When present, such ethoxylated amines may be used in any effective amount.

In particular, when present, the friction modifier(s) can comprise or be a glycerol monooleate, an ester (e.g., tallow ester) of triethanolamine (TEEMA), an ester (e.g., tallow ester) of a succinic anhydride having an $R^{14}$ hydrocarbyl substitution, an $R^{14}/R^{15}$-functionalized polyethylene polyamine succinimide, an ethoxylated amine in which $R^{19}$ and/or $R^{20}$ contain 16 to 20 carbon atoms, or a combination thereof When present, useful concentrations of friction modifiers may range from 0.01 to 8 mass %, e.g., from 0.05 to 6.5 mass % or from 0.1 to about 5 mass %. While organomolybdenum compounds may sometimes be categorized as friction modifiers, they are categorized herein as antiwear agents and, thus for accounting purposes, excluded from percentages reflecting friction modifier components in additive packages and/or lubricating oil compositions. Friction modifiers of all types may be used alone or in mixtures with the materials of this disclosure. Mixtures of two or more friction modifiers, or mixtures of a friction modifier with alternate surface-active material(s), may additionally or alternatively be desirable.

Antiwear Agents

Molybdenum-Containing Compounds

In some embodiments, the additive package and/or the lubricating oil composition may further comprise one or more oil-soluble or oil-dispersible molybdenum-containing compounds, such as an oil-soluble or oil-dispersible organo-molybdenum compound. In other embodiments, the additive package and/or the lubricating oil composition may further comprise substantially no oil-soluble or oil-dispersible molybdenum-containing compounds.

Non-limiting examples of such oil-soluble or oil-dispersible organo-molybdenum compound may include, but are not necessarily limited to, molybdenum dithiocarbamates, molybdenum dithiophosphates, molybdenum dithiophosphinates, molybdenum xanthates, molybdenum thioxanthates, molybdenum sulfides, and the like, and mixtures thereof, in particular one or more of molybdenum dialkyldithiocarbamates, molybdenum dialkyldithiophosphates, molybdenum alkyl xanthates, and molybdenum alkylthioxanthates. Representative molybdenum alkyl xanthate and molybdenum alkylthioxanthate compounds may be expressed using the formulae of $Mo(R_{21}OCS_2)_4$ and $Mo(R_{21}SCS_2)_4$, respectively, wherein each $R_{21}$ may independently be an organo group selected from the group consisting of alkyl, aryl, aralkyl, and alkoxyalkyl, generally having from 1 to 30 carbon atoms or from 2 to 12 carbon atoms, in particular each being an alkyl group having from 2 to 12 carbon atoms.

In some embodiments, the oil-soluble or oil-dispersible organo-molybdenum compound may comprise a molybdenum dithiocarbamate, such as a molybdenum dialkyldithiocarbamate, and/or may be substantially free from molybdenum dithiophosphates, in particular from molybdenum dialkyldithiophosphates. In some embodiments, any oil-soluble or oil-dispersible molybdenum compounds may consist of a molybdenum dithiocarbamate, such as a molybdenum dialkyldithiocarbamate, and/or a molybdenum dithiophosphate, such as a molybdenum dialkyldithiophosphate, as the sole source(s) of molybdenum atoms in the composition. In either set of embodiments, when present, the oil-soluble or oil-dispersible molybdenum compound may consist essentially of a molybdenum dithiocarbamate, such as a molybdenum dialkyldithiocarbamate, as the sole source of molybdenum atoms in the lubricating oil composition.

The molybdenum compound, when present, may be mono-, di-, tri-, or tetra-nuclear, in particular comprising or being di-nuclear and/or tri-nuclear molybdenum compounds.

Suitable dinuclear or dimeric molybdenum dialkyldithiocarbamates, for example, can be represented by the following formula:

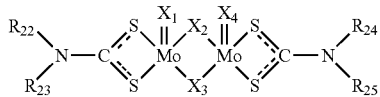

where $R_{22}$ through $R_{25}$ may each independently represent a straight chain, branched chain, or aromatic hydrocarbyl group having 1 to 24 carbon atoms, and where $X_1$ through $X_4$ may each independently represent an oxygen atom or a sulfur atom. The four hydrocarbyl groups, $R_{22}$ through $R_{25}$, may be identical to, or different from, each other.

Suitable tri-nuclear organo-molybdenum compounds may include those having the formula: $Mo_3S_kL_nQ_z$, and mixtures thereof. In such tri-nuclear formula, the three molybdenum atoms may be linked to multiple sulfur atoms (S), with k varying from 4 through 7. Additionally, each L may be an independently selected organic ligand having a sufficient number of carbon atoms to render the compound oil-soluble or oil-dispersible, with n being from 1 to 4. Further, when z is non-zero, Q may be selected from the group of neutral electron-donating compounds such as water, amines, alcohols, phosphines, and/or ethers, with z ranging from 0 to 5 and including non-stoichiometric (non-integer) values.

In such tri-nuclear formula, at least 21 total carbon atoms (e.g., at least 25, at least 30, or at least 35) may typically be present among the combination of all ligands ($L_n$). Importantly, however, the organic groups of the ligands may advantageously collectively exhibit a sufficient number of carbon atoms to render the compound soluble or dispersible in the oil. For example, the number of carbon atoms within each ligand L may generally range from 1 to 100, e.g., from 1 to 30 or from 4 to 20.

Tri-nuclear molybdenum compounds having the formula $Mo_3S_kL_nQ_z$ may advantageously exhibit cationic cores surrounded by anionic ligands, such as represented by one or both of the following structures:

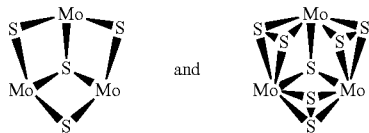

Such cationic cores may each have a net charge of +4 (e.g., due to the oxidation state of the Mo atoms each being +4). Consequently, in order to solubilize these cores, the total charge among all the ligands should correspond, in this case being −4. Four mono-anionic ligands may offer an advantageous core neutralization. Without wishing to be bound by any theory, it is believed that two or more tri-nuclear cores may be bound or interconnected by means of one or more ligands, and the ligands may be multidentate. This includes the case of a multidentate ligand having multiple connections to a single core. Oxygen and/or selenium may be substituted for some portion of the sulfur atoms in either of the cores.

As ligands for the tri-nuclear cores described above, non-limiting examples may include, but are not necessarily limited to, dithiophosphates such as dialkyldithiophosphate, xanthates such as alkylxanthate and/or alkylthioxanthate, dithiocarbamates such as dialkyldithiocarbamate, and combinations thereof, in particular each comprising or being dialkyldithiocarbamate. Additionally, or alternatively, the ligands for the tri-nuclear molybdenum-containing cores may independently be one or more of the following:

$$----X_5-R_{26}$$

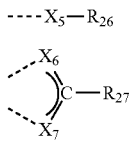

-continued

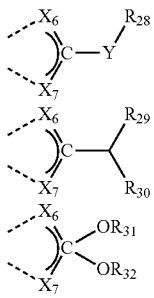

where $X_5$, $X_6$, $X_7$, and Y are each independently oxygen or sulfur, where Z is nitrogen or boron, and wherein $R_{26}$, $R_{27}$, $R_{28}$, $R_{29}$, $R_{30}$, $R_{31}$, and $R_{32}$ are each independently hydrogen or an organic (carbon-containing) moiety, such as a hydrocarbyl group, that may be the same or different from each other, in particular the same. Exemplary organic moieties may include or be alkyl (e.g., in which the carbon atom attached to the remainder of the ligand is primary or secondary), aryl, substituted aryl, alkaryl, substituted alkaryl, aralkyl, substituted aralkyl, an ether, a thioether, or a combination or reaction product thereof, in particular alkyl.

Oil-soluble or oil-dispersible tri-nuclear molybdenum compounds can be prepared by reacting in the appropriate liquid(s)/solvent(s) a molybdenum source such as $(NH_4)_2Mo_3S_{13}\cdot n(H_2O)$, where n varies from 0 to 2 including non-stoichiometric (non-integer) values, with a suitable ligand source, such as a tetralkylthiuram disulfide. Other oil-soluble or dispersible tri-nuclear molybdenum compounds can be formed during a reaction in the appropriate solvent(s) of a molybdenum source such as of $(NH_4)_2Mo_3S_{13}\cdot n(H_2O)$, a ligand source, such as tetralkylthiuram disulfide, a dialkyldithiocarbamate, or a dialkyldithiophosphate, and a sulfur abstracting agent, such as cyanide ions, sulfite ions, or substituted phosphines. Alternatively, a tri-nuclear molybdenum-sulfur halide salt such as $[M']_2[Mo_3S_7A_6]$, where M' is a counter ion and A is a halogen such as Cl, Br, or I, may be reacted with a ligand source such as a dialkyldithiocarbamate or a dialkyldithiophosphate in an appropriate liquid/solvent (system) to form an oil-soluble or oil-dispersible trinuclear molybdenum compound. The appropriate liquid/solvent (system) may be, for example, aqueous or organic.

Other molybdenum precursors may include acidic molybdenum compounds. Such compounds may react with a basic nitrogen compound, as measured by ASTM D664 or D2896 titration procedure and may typically be hexavalent. Examples may include, but are not necessarily limited to, molybdic acid, ammonium molybdate, sodium molybdate, potassium molybdate, and other alkaline metal molybdates and other molybdenum salts, e.g., hydrogen sodium molybdate, $MoOCl_4$, $MoO_2Br_2$, $Mo_2O_3Cl_6$, molybdenum trioxide, or similar acidic molybdenum compounds, or combinations thereof. Thus, additionally or alternatively, the concentrates and/or compositions of the present disclosure can be provided with molybdenum, when desired, by molybdenum/sulfur complexes of basic nitrogen compounds as described, for example, in U.S. Pat. Nos. 4,263,152; 4,285,822; 4,283,295; 4,272,387; 4,265,773; 4,261,843; 4,259,195; and 4,259,194; and/or in PCT Publication No. WO 94/06897.

When present, molybdenum-containing compounds may be present in the lubricating oil composition in an amount from 0.1 to 2.0% by mass, based on the total mass of the composition, from 0.1 to 1.5% by mass, from 0.2 to 1.2% by mass, or from 0.2% to 0.8% by mass. Additionally, or alternatively, when present, molybdenum-containing compounds may provide the lubricating oil composition with from 50 to 1500 parts per million by mass of molybdenum, based on the total mass of the composition, e.g., from 75 to 800 ppm, from 100 to 500 ppm, or from 300 to 1200 ppm. Molybdenum content can be measured in accordance with ASTM D5185.

Although molybdenum-containing compounds may have other functions and may be alternatively classified, e.g., as antioxidants and/or friction modifiers, molybdenum-containing compounds are classified herein as antiwear agents. Therefore, compositions that are characterized as being substantially free of antiwear agents should be understood to contain substantially no molybdenum-containing compounds, despite their other potential functional additive characteristics. Similarly, compositions that are characterized as being substantially free of friction modifiers may nonetheless contain these molybdenum-containing compounds. Nevertheless, additive packages and/or lubricating oil compositions containing molybdenum-containing compounds may still be substantially free of other antiwear agents.

Zinc-Based Phosphorus-Containing Compounds

In some embodiments, the additive package and/or the lubricating oil composition may further comprise one or more zinc-based phosphorus-containing compounds, such as one or more zinc dihydrocarbyl dithiophosphate compounds. Such compounds are known in the art and often referred to as ZDDP. In other embodiments, the additive package and/or the lubricating oil composition may further comprise substantially no zinc-based phosphorus-containing compounds.

ZDDP compounds may be prepared in accordance with known techniques, such as by first forming a dihydrocarbyl dithiophosphoric acid (DDPA), usually by reaction of one or more alcohols or a phenol with $P_2S_5$, and then neutralizing the formed DDPA with a zinc compound. For example, a dithiophosphoric acid may be made by reacting mixtures of primary and secondary alcohols. Alternatively, dithiophosphoric acids can be prepared where the hydrocarbyl groups are entirely secondary in character or the hydrocarbyl groups are entirely primary in character. To make the zinc salt, any basic or neutral zinc compound may be used, but oxides, hydroxides, and carbonates are typically employed. Commercial additives, when used, may frequently contain an excess of zinc, due to the use of an excess of the basic zinc compound in the neutralization reaction.

Advantageous zinc dihydrocarbyl dithiophosphates may comprise or be oil-soluble or oil-dispersible salts of dihydrocarbyl dithiophosphoric acids, such as represented by the following formula:

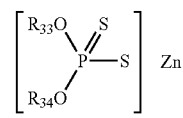

wherein $R_{33}$ and $R_{34}$ may be the same or different hydrocarbyl radicals containing from 1 to 18 (e.g., from 2 to 12 or from 2 to 8) carbon atoms, examples of which hydrocarbyl radicals may include one or more of alkyl, alkenyl, aryl, arylalkyl, alkaryl, and cycloaliphatic radicals. Exemplary hydrocarbyl radicals may comprise or be, but are not necessarily limited to, ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, benzyl, butylphenyl, cyclohexyl, methylcyclopentyl, propenyl, butenyl, and combinations thereof. In order to obtain and/or maintain adequate oil solubility, the total number of carbon atoms on each dihydrocarbyl dithiophosphoric acid ligand (i.e., a single $R_{33}$ and $R_{34}$ pair) may generally be at least 3, or at least 5. In particular, the zinc dihydrocarbyl dithiophosphate can therefore comprise or be a zinc dialkyl dithiophosphate. However, aryl, aralkyl, and/or alkaryl hydrocarbyl groups may be partially or completely substituted for the alkyl/alkenyl groups listed above.

The carbon atom on the hydrocarbyl radicals attached to the oxygen may be all primary carbons, all secondary carbons, or a mixture of primary and secondary carbons; typically, at least some such carbon atoms are secondary carbons. Secondary ZDDP compounds are available commercially, e.g., from Lubrizol under the trade designations "LZ 677A", "LZ 1095", and "LZ 1371", from Chevron Oronite under the trade designation "OLOA 262", and from Afton Chemical under the trade designation "HITEC™ 7169", inter alia.

When desired, one or more ZDDP compounds may be present in the lubricating oil composition in an amount from 0.4 to 5.0% by mass, based on the total mass of the composition, e.g., from 0.6 to 3.5% by mass, from 1.0 to 3.0% by mass, or from 1.2 to 2.5% by mass. Additionally, or alternatively, when present, ZDDP compounds may individually provide the lubricating oil composition with from 300 to 4000 parts per million by mass of phosphorus, based on the total mass of the composition, e.g., from 500 to 2500 ppm, from 750 to 2000 ppm, or from 800 to 1600 ppm. Further, additionally or alternatively, when present, ZDDP compounds may provide the lubricating oil composition with from 400 to 4500 parts per million by mass of zinc, based on the total mass of the composition, e.g., from 500 to 3000 ppm, from 800 to 2600 ppm, or from 1000 to 2200 ppm. Zinc and phosphorus content can each be measured in accordance with ASTM D5185.

Additionally, or alternatively, one or more of zinc dihydrocarbyl dithiocarbamates, zinc alkanoates (e.g., zinc stearate, zinc isostearate, zinc palmitate, zinc myristate, zinc laurate, zinc caprate, zinc 2-ethylhexanoate, and the like), zinc alkenoates (e.g., zinc oleate and/or zinc undecylenate), and zinc aryl, aralkyl, and/or alkaryl compounds (e.g., zinc benzoate, zinc phenate, and/or zinc naphthenate) can be used as antiwear agents.

Ashless Phosphorus-Containing Compounds

Ashless antiwear agents may represent individual compounds or mixtures of compounds. In one embodiment comprising an ashless antiwear mixture of compounds, the ashless antiwear mixture can comprise a component (i) and a component (ii). Component (i) may advantageously have significant antiwear properties, while component (ii) may or may not have antiwear properties.

Ashless antiwear component (i) may advantageously comprise a mixture of two or more compounds of the structures (II):

where groups $R_{35}$, $R_{36}$, and $R_{37}$ may each independently comprise or be hydrocarbyl groups having 1 to 18 carbon atoms and/or hydrocarbyl groups having 1 to 18 carbon atoms where the alkyl chain is interrupted by a thioether linkage, with the proviso that at least some of the set of all groups collectively representing $R_{35}$, $R_{36}$, and $R_{37}$ may comprise or be hydrocarbyl groups having 1 to 18 carbon atoms where the alkyl chain is interrupted by a thioether linkage. The mixture may comprise three or more, four or more, or five or more compounds of the structures (II).

In some embodiments, groups $R_{35}$, $R_{36}$, and $R_{37}$ may each independently comprise or be hydrocarbyl (in particular alkyl) groups having 4 to 10 carbon atoms and/or hydrocarbyl (in particular alkyl) groups having 4 to 10 carbon atoms where the alkyl chain is interrupted by a thioether linkage, with the proviso that at least some groups from the set of all groups $R_{35}$, $R_{36}$, and $R_{37}$ collectively may comprise or be hydrocarbyl (in particular alkyl) groups having 4 to 10 carbon atoms where the hydrocarbyl (in particular alkyl) chain is interrupted by a thioether linkage.

When groups $R_{35}$, $R_{36}$, and $R_{37}$ comprise alkyl groups (in which the alkyl chain is not interrupted by a thioether linkage), examples may include but are not limited to methyl, ethyl, propyl, and butyl, in particular including or being butyl.

When groups $R_{35}$, $R_{36}$, and $R_{37}$ comprise hydrocarbyl (in particular alkyl) groups where the hydrocarbyl (in particular alkyl) chain is interrupted by a thioether linkage, examples include groups of the structure —R'—S—R" where R' may be —$(CH_2)_n$—, in which n may be an integer from 2 to 4, and where R" may be —$(CH_2)_m$—$CH_3$, in which m may be an integer from 1 to 15, such as from 1 to 7.

In particular, in the mixture of compounds of structure (II) comprising component (i), at least 10% (e.g., at least 20%, at least 30%, or at least 40%) by mass of the mixture comprises compounds of structure (II) in which at least one of $R_{35}$, $R_{36}$, and $R_{37}$ (as applicable, in each compound) comprises or is an alkyl group where the alkyl chain is interrupted by a thioether linkage, particularly having the structure —R'—S—R", where R' may be —$(CH_2)_n$—, in which n may be an integer from 2 to 4, and where R" may be —$(CH_2)_m$—$CH_3$, in which m may be an integer from 1 to 15, such as from 1 to 7.

Ashless antiwear component (ii) may advantageously comprise one or more compounds of structures (III):

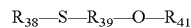

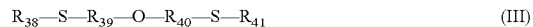

where groups $R_{38}$ and $R_{41}$ may each independently comprise or be alkyl groups having 1 to 12 carbon atoms, and where $R_{39}$ and $R_{40}$ may each independently comprise or be alkyl linkages having 2 to 12 carbon atoms. In particular, $R_{38}$ and $R_{41}$ may each independently comprise or be —$(CH_2)_m$—$CH_3$, where m is an integer from 1 to 15, such as from 1 to 7, and $R_{39}$ and $R_{40}$ (if present) may each independently comprise or be —$(CH_2)_n$—, where n is an integer from 2 to

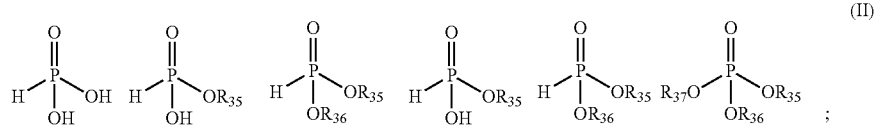

4. The mixture may comprise two or more or three or more compounds of the structures (III).

In particular, when present, compounds of structure (II) [Component (i)] and compounds of structure (III) [Component (ii)] may each be present in the lubricating oil composition in an amount from 0.04 to 1.0% by mass, based on the total mass of the composition, e.g., from 0.05 to 0.8% by mass, from 0.05 to 0.5% by mass, or from 0.07 to 0.4% by mass. Additionally, or alternatively, in particular, compounds of structure (II) [Component (i)] and compounds of structure (III) [Component (ii)] may collectively provide the lubricating oil composition with from 80 to 800 parts per million by mass of phosphorus, based on the total mass of the composition, e.g., from 100 to 700 ppm, from 150 to 600 ppm, or from 200 to 500 ppm. Phosphorus content can be measured in accordance with ASTM D5185. Further, additionally or alternatively, in particular, when present, a mass ratio of compounds of structure (II) [Component (i)] and compounds of structure (III) [Component (ii)] may be from 2:1 to 1:2, from 5:3 to 3:5, from 3:2 to 2:3, or from 4:3 to 3:4.

Individual examples of ashless antiwear agents can include one or more compounds from structures (II) above, such that alternative mixtures of ashless antiwear agents can include simply two or more compounds from structures (II) above, even in the absence of structures (III) of component (ii). Antiwear agents may, additionally or alternatively, comprise mixtures of one or more ashless antiwear agents and one or more metal-containing antiwear agents.

Anti-Foam Agents

Anti-foam agents (anti-foamants) may advantageously be added to the additive packages/concentrates and/or lubricant oil compositions according to the present disclosure, if desired, e.g., to retard formation of stable foams. Silicones and certain organic polymers are typical anti-foamants. For example, polysiloxanes such as silicon oil (e.g., polydimethyl siloxane) may provide anti-foam properties in appropriate proportions. Anti-foamants are commercially available and, when present, may be used in minor amounts, such as less than 1 mass % and often less than 0.1 mass %.

Viscosity Modifiers

Viscosity modifiers (also referred to as viscosity index improvers/VIIs or viscosity improvers) may be included in the lubricating compositions described herein. Viscosity modifiers provide lubricants with high and low temperature operability. These additives may impart shear stability at elevated temperatures and acceptable viscosity at low temperatures. Suitable viscosity modifiers may include high molecular weight hydrocarbons, polyesters, and viscosity modifier dispersants that can function as both a viscosity modifier and a dispersant. Typical molecular weights of these polymers can be from about 10 to 1500 kiloDaltons (kD), e.g., from about 20 to 1200 kD or from about 50 to 1000 kD.

Examples of suitable viscosity modifiers can include linear or star-shaped polymers and copolymers of methacrylate, butadiene, olefins, and/or optionally alkylated styrenes. Polyisobutylene is a commonly used viscosity modifier. Another suitable viscosity modifier class is poly(meth)acrylate (copolymers of various chain length alkyl (meth)acrylates, for example), some formulations of which may also/alternatively serve as pour point depressants (below). Other suitable viscosity modifiers may include copolymers of ethylene and propylene, copolymer of ethylene and higher carbon number comonomers, and/or hydrogenated block copolymers of styrene and dienes such as butadiene and/or isoprene. Specific examples may include styrene-isoprene or styrene-butadiene based polymers of 50 to 200 kD molecular weight. Copolymers useful as viscosity modifiers may include those commercially available from Chevron Oronite under the trade designation PARATONE™ (such as PARATONE™ 8921, PARATONE™ 68231, and PARATONE™ 8941); from Afton Chemical under the trade designation HiTEC™ (such as HiTEC™ 5850B); and from Lubrizol under the trade designation Lubrizol™ 7067C. Hydrogenated polyisoprene star polymers (including diblock/multiblock arms containing styrene and isoprene blocks) useful as viscosity modifiers herein may include those commercially available from Infineum International Limited, e.g., under trade designations SV200™ and SV600™. Hydrogenated diene-styrene block copolymers useful as viscosity modifiers herein are commercially available from Infineum International Limited, e.g., under the trade designation SV50™.

Polymers useful as viscosity modifiers herein may include polymethacrylate or polyacrylate polymers, such as linear poly(meth)acrylate polymers, such as those available from Evonik Industries under the trade designation Viscoplex™ (e.g., Viscoplex™ 6-954), or star polymers such as available from Lubrizol under the trade designation Asteric™ (e.g., Lubrizol™ 87708 and Lubrizol™ 87725).

Vinyl aromatic-containing polymers useful as viscosity modifiers herein may be derived from vinyl aromatic hydrocarbon monomers, such as styrenic monomers, e.g., styrene. Illustrative vinyl aromatic-containing copolymers useful herein may be represented by the general formula A-B, wherein A is a polymeric block derived predominantly from vinyl aromatic hydrocarbon monomer (such as styrene), and B is a polymeric block derived predominantly from conjugated diene monomer (such as butadiene and/or isoprene).

When used/desired, the viscosity modifiers may be incorporated into lubricant oil compositions (formulations) in an amount from about 0.01 to about 10 mass %, such as from about 0.1 to about 7 mass %, from about 0.1 to about 4 mass %, from about 0.2 to about 2 mass %, from about 0.2 to about 1 mass %, or from about 0.2 to about 0.5 mass %, based on the total mass of the composition/formulation. While the viscosity modifiers may be added either into an additive package concentrate or may be mixed into a lubricant formulation during/after dilution, the amounts above reflect the amount present in the ultimate lubricant formulation, and corresponding amounts that may be present if the VMs are added into an additive package concentrate can easily be back-calculated, e.g., assuming that the concentrate represents from about 5% to about 20% by mass of the final formulation Viscosity modifier components typically exist as concentrates, in basestock/diluent oil typically similar to that in the additive package concentrate and/or the lubricant oil composition/formulation. The "as delivered" viscosity modifier can typically contain from 20 mass % to 75 mass % of an active polymer for polymethacrylate or polyacrylate polymers, or from 8 mass % to 25 mass % of an active polymer for olefin copolymers, hydrogenated polyisoprene star polymers, or hydrogenated diene-styrene block copolymers, in the "as delivered" component/concentrate form.

Pour Point Depressants

Conventional pour point depressants (PPDs, a.k.a. lubricant oil flow improvers or LOFIs) may be added to the additive packages/concentrates and/or lubricant oil compositions according to the present disclosure, if desired, e.g., to lower the minimum temperature at which the fluid will flow or can be poured. Examples of suitable pour point depressants may include polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. U.S. Pat. Nos. 1,815,022; 2,015,748; 2,191,498; 2,387,501; 2,655,479; 2,666,746; 2,721,877; 2,721,878; and 3,250,715 describe pour point depressants and/or the preparation thereof. When present in additive packages/concentrates and/or lubricant oil compositions according to the present disclosure, such additives may be used in an amount of about 0.01 to 5 mass %, e.g., about 0.01 to 1.5 mass %.

Other Additives

Other additives known in the art may optionally be added to the additive packages/concentrates and/or lubricant oil compositions according to the present disclosure, such as other friction modifiers, other antiwear agents, demulsifiers, anti-foaming agents, tackifiers (e.g., hydrocarbyl/oligomeric/polymeric succinic anhydrides), extreme pressure agents, seal compatibility (swell) agents, and the like. A variety of additive categories (genera) and additive compounds (species) are disclosed in, for example, "Lubricant Additives" by C. V. Smallheer and R. Kennedy Smith, 1967, pp 1-11.

Additional Embodiments

Additionally, or alternatively, the present disclosure may include one or more of the following embodiments:

Embodiment 1. An overbased alkaline earth metal hydrocarbyl-substituted salicylate detergent comprising both carbonate and borate moieties and exhibiting the following characteristics: a basicity index of at least 3.8; a ratio of soap content to mass % boron is greater than 55 mmol/kg; a soap content of at least 330 mmol/kg; a TBN, measured according to ASTM D2896, of at least 220 mg KOH/g; and a mass ratio of borate to carbonate from 0.75 to 6.0, wherein the alkaline earth metal comprises calcium and/or magnesium, and the hydrocarbyl substitution comprises 9 to 30 carbon atoms.

Embodiment 2. An overbased calcium salicylate detergent according to embodiment 1, wherein at least three, at least four, or all five of the following are satisfied: the basicity index is not greater than 9.0; the ratio of soap content to mass % boron is less than 300 mmol/kg; the TBN, measured according to ASTM D2896, is at most 500 mg KOH/g; the soap content is at most 550 mmol/kg; and the hydrocarbyl substitution comprises a $C_{14}$ to $C_{24}$ alkyl or alkenyl moiety.

Embodiment 3. An overbased calcium salicylate detergent according to embodiment 1 or embodiment 2, which exhibits a boron content, according to ASTM D4951, of at least 3.2% by mass.

Embodiment 4. An overbased calcium salicylate detergent according to any one of the previous embodiments 1 to 3, wherein the mass ratio of borate to carbonate is from 1.0 to 5.0.

Embodiment 5. An overbased calcium salicylate detergent according to any one of the previous embodiments 1 to 4, which exhibits an alkaline earth metal content, according to ASTM D4951, of at least 7.0% by mass.

Embodiment 6. An overbased calcium salicylate detergent according to any one of the previous embodiments 1 to 5, which exhibits a mass ratio of alkaline earth metal to boron is from 1.5 to 5.5.

Embodiment 7. An overbased calcium salicylate detergent according to any one of the previous embodiments 1 to 6, wherein: the basicity index is from 5.0 to 8.3; the ratio of soap content to mass % boron is between 70 and 275 mmol/kg; the TBN, measured according to ASTM D2896, is from 265 to 350 mg KOH/g; the combined calcium and magnesium content, according to ASTM D4951, is from 7.0% to 12.5% by mass; the boron content, according to ASTM D4951, is from 3.5% to 6.8% by mass; the soap content is from 350 to 520 mmol/kg; the mass ratio of alkaline earth metal to boron is from 1.7 to 4.5; the mass ratio of borate to carbonate moieties is from 1.6 to 3.0; and the hydrocarbyl substitution comprises a $C_{14}$ to $C_{19}$ alkyl or alkenyl moiety.

Embodiment 8. A method for making a substantially package-stable overbased alkaline earth metal hydrocarbyl-substituted salicylate detergent comprising both carbonate and borate moieties, the method comprising the steps of: providing an oil-soluble or oil-dispersible overbased but unborated alkaline earth metal hydrocarbyl-substituted salicylate detergent made by reacting a mineral oil solution of an acid with a stoichiometric excess of a neutralizing agent comprising an alkaline earth metal carbonate or bicarbonate, optionally in the presence of promoter, at a temperature from 60 to 200° C. for a sufficient period of time to have thereby formed the overbased but unborated alkaline earth metal hydrocarbyl-substituted salicylate detergent, which exhibits a basicity index of at least 3.5, a soap content of at least 330 mmol/kg, an alkaline earth metal content, measured according to ASTM D4951, of at least 7.0% by mass, and a TBN, according to ASTM D2896, of at least 240 mg KOH/g, wherein the alkaline earth metal comprises calcium and/or magnesium, wherein the overbased but unborated alkaline earth metal hydrocarbyl-substituted salicylate detergent comprises carbonate moieties, and wherein the hydrocarbyl substitution comprises 9 to 30 carbon atoms; admixing said overbased but unborated alkaline earth metal hydrocarbyl-substituted salicylate detergent in an organic diluent medium comprising an aprotic hydrocarbon solvent and a $C_1$-$C_4$ primary alcohol but comprising no intentionally added water with a boron source at a temperature below 100° C. to form a reaction mixture; heating the reaction mixture to a temperature from 105° C. to 225° C. at a heating rate below 3° C./min in a borating process to form a crude borated detergent product; optionally further adding additional aprotic hydrocarbon solvent, thereby still forming a crude borated detergent product; and removing a significant portion of the diluent medium, as well as water, formed during the borating process, in order to form the overbased alkaline earth metal hydrocarbyl-substituted salicylate detergent according to any one of the previous embodiments 1 to 7.

Embodiment 9. The method according to embodiment 8, wherein: the aprotic hydrocarbon solvent comprises benzene, xylene, toluene, mesitylene, naphthalene, cyclohexane, cyclooctane, heptane, octane, decane, dodecane, or a combination thereof; the boron source comprises orthoboric acid, metaboric acid, tetraboric acid, monoammonium borate, diammonium borate, triammonium borate, $C_1$-$C_4$ alkyl dihydrogen borate, di-$C_1$-$C_4$ alkyl hydrogen borate, tri-$C_1$-$C_4$ alkyl borate, or a combination thereof; or both.

Embodiment 10. A lubricant additive package concentrate comprising: less than 40% by mass of a Group I, Group II, and/or Group III lubricating oil basestock; at least 0.5% by mass of the boron-containing overbased calcium salicylate detergent according to any one of embodiments 1-7 and/or made according to the method of any one of embodiments 8-9; at least one ashless dispersant; at least one antioxidant; at least one friction modifier; and optionally one or more of an additional detergent, a corrosion inhibitor, an antiwear agent, a seal swelling agent, an anti-foamant, an extreme pressure agent, a viscosity modifier, and a pour point depressant.

Embodiment 11. A lubricant additive package concentrate according to embodiment 10, wherein the at least one friction modifier comprises a substantially sulfur-free ashless organic friction modifier.

Embodiment 12. A lubricant additive package concentrate according to embodiment 10, wherein the at least one friction modifier comprises a substantially nitrogen-free and substantially sulfur-free ashless organic friction modifier.

Embodiment 13. A lubricant additive package concentrate according to any one of embodiments 10-12, which exhibits package stability at ~60° C. for at least 12 weeks.

Embodiment 14. A lubricating oil composition comprising: at least 70% by mass of a lubricating oil basestock comprising one or more of Group I, Group II, Group III, and/or Group IV basestocks; and at least 5% by mass of the lubricant additive package concentrate according to any one of embodiments 10-13.

Embodiment 15. A lubricating oil composition comprising: at least 85% by mass of a lubricating oil basestock comprising one or more of Group I, Group II, Group III, and/or Group IV basestocks; at least 0.05% by mass of the boron-containing overbased calcium salicylate detergent according to any one of embodiments 1-7 and/or made according to the method of any one of embodiments 8-9; at least one ashless dispersant; at least one antioxidant; at least one friction modifier; and optionally one or more of an additional detergent, a corrosion inhibitor, an antiwear agent, a seal swelling agent, a tackifier, a demulsifier, an anti-foamant, an extreme pressure agent, a viscosity modifier, and a pour point depressant.

Embodiment 16. The use of an overbased calcium salicylate detergent according to any one of embodiments 1-7, an overbased alkaline earth metal hydrocarbyl-substituted salicylate detergent produced according to the method of embodiments 8 or 9, or a lubricant additive package concentrate according to any one of embodiments 10-12 to obtain package stability at ~60° C. for at least 12 weeks.

The invention will now be described by way of non-limiting examples only.

EXAMPLES

Borated Detergent Synthesis

Comparative Example A1 is the borated detergent synthesis example from column 22 of U.S. Pat. No. 10,584,300. The example is reproduced herein. A reactor flask equipped with Dean-Stark trap was charged with 1 kg overbased calcium salicylate having a TBN of 225 mgKOH/g and 1 kg of xylene. With stirring and under nitrogen, 124 g of boric acid was added slowly at room temperature. The temperature was then raised to 115° C. over 2 hours, then held at 115° C. for 1 hour after. The reaction mixture was then heated to 140° C. over 90 minutes followed by a 40-minute hold at 140° C. The reaction mixture was then cooled, and the mixture centrifuged before concentration in vacuo on a rotary evaporator to afford approximately 1 kg of borated calcium salicylate product. ICP analysis (measured according to ASTM D4951) showed the product to have 3.09% boron and 6.77% calcium by mass. The product had a TBN (measured according to ASTM D2896) of 186 mg KOH/g. A calculation of the basicity index (metal ratio) from this Comparative Example yields a value of ~3. The product was estimated to have a ratio of soap content to mass % boron of approximately 182 mmol/kg and a soap content of approximately 563 mmol/kg. The hydrocarbyl substitution of the product comprised a mixture of 14 to 18 carbon atoms.

Comparative Example A2 is inventive Example 1 from U.S. Pat. No. 5,380,508 ("the '508 patent"). The example is reproduced herein. Two hundred (200) grams of a neutral calcium alkylsalicylate (calcium content; 2.0 wt. %)(A), which had been diluted to an extent of effective concentration of 50% by mass with a lubricating oil fraction, 26 g of calcium hydroxide (B), 43.4 g (2.0 moles per mole of calcium hydroxide) of orthoboric acid (C) and 400 g of xylene (F) were put in a 1000-mL four-necked flask fitted with a condenser and heated to 60° C. while agitating. To this mixture were added 120 g of methanol (D) and 20 g of water (E), and the resulting mixture was heated up to a refluxing temperature (66° C.) under agitation and reacted for 4 hours. The reaction mixture was further heated to 140° C. for 1.5 hours to distill out the methanol, water, and xylene. Finally, the reaction product was diluted twofold with hexane and filtered to remove any residual solids present, and the hexane was distilled out to obtain a desired calcium borate overbased alkylsalicylate. It should be noted that, in this Comparative Example, a neutral calcium detergent was used as a starting material, and the calcium overbasing and borating steps were accomplished simultaneously. The product had a TBN of 205 mg KOH/g; a boron content of 3.1% by mass; a calcium content of 7.0% by mass and the hydrocarbyl substitution comprised a mixture of 16 and 18 carbon atoms.

According to the '508 patent, the results obtained by the transmission-type electron microscopic observation of the thus obtained calcium borate overbased alkylsalicylate showed that the calcium borate which was an overbasic component had a particle diameter of not more than 50 Angstroms. Further, 5% by mass of water and 1% by mass of methanol were added to the calcium borate overbased alkylsalicylate to obtain a mixture which was agitated at 93.5° C. for 24 hours with the use of an apparatus prescribed in ASTM D2619 to precipitate the calcium borate which was an overbasic component and dispersed in the mixture and then centrifuged to collect precipitated calcium borate. The thus collected calcium borate was measured with an X-ray analyzer with the result that it was found to be meta-calcium borate.

Table A of the '508 patent also shows for this detergent a calculated Base Number of 200 (205, as measured according ASTM D664), a calcium content of 7.0 mass %, a boron content of 3.1 mass %, and a calculated B/Ca molar ratio of 1.6 [the analyzed. B/Ca molar ratio value of 2.1 was based on the addition of extra methanol and water, in an attempt to detach and isolate calcium borate from the detergent—standard measurements of inorganic contents usually encapsulate the entire reaction product, instead of attempting to isolate the inorganic portion from the (semi-)organic portion of the detergent component].

Comparative Example A3 is Comparative Example 2 from U.S. Pat. No. 5,380,508 ("the '508 patent"). The example is reproduced herein. Two hundred (200) grams of the same neutral calcium alkylsalicylate (A) as used in Comparative Example A1, 26 g of calcium hydroxide (B), 43.4 g (2.0 moles per mole of the calcium hydroxide) of orthoboric acid (C), and 400 g of xylene (F) were put in a 1000-ml four-necked flask fitted with a condenser and heated to 60° C. while agitating. To this mixture was added 120 g of methanol, and the resulting mixture was heated up to a refluxing temperature (66° C.) under agitation and reacted for 4 hours to obtain a reaction product. The reaction product was further heated to 140° C. for 1.5 hours to distill out the methanol, reaction water, and xylene. Finally, the reaction product was diluted twofold with hexane and filtered to remove any residual solids present, and the hexane was distilled out to obtain a calcium borate overbased alkylsalicylate. However, the thus obtained calcium borate overbased alkylsalicylate caused its gelation and was found generally unusable as an additive for petroleum products. The hydrocarbyl substitution of the product comprised a mixture of 16 and 18 carbon atoms.

In Example A4, a reactor flask was charged with ~395 g of overbased (carbonated) calcium salicylate having a TBN of ~350 mg KOH/g, a soap content over 500 mmol/kg, and a basicity index of ~6, —395 g of xylene, and ~156 g of methanol. The mixture was heated to ~40° C. with stirring, and, under nitrogen, ~178 g of boric acid was added over approximately 1 hour. The temperature was then raised to ~140° C. over ~135 more minutes. The reaction mixture was then cooled to below ~100° C. before diluting with an additional ~262 g of xylene, and then cooling was continued. After cooling, the mixture was centrifuged and concentrated in vacuo on a rotary evaporator at ~140° C. over ~2 hours (to remove diluents, reaction water, and other volatile components) to yield a borated overbased calcium salicylate product. ICP analysis (measured according to ASTM D4951) showed the product to have ~5.14% boron and 10.51% calcium by mass. The borated product had a TBN (measured according to ASTM D2896) of ~298 mg KOH/g and a basicity index (metal ratio) of ~5.84. The product had a ratio of soap content to mass % boron of 87 mmol/kg; a soap content of 443 mmol/kg; and a mass ratio of borate to carbonate of 1.6. The hydrocarbyl substitution of the product comprised a mixture of 14 to 18 carbon atoms.

The mass ratio of borate-to-carbonate of 1.6 for Example A4 was determined as follows. Firstly, the total base number (TBN) of the detergent sample was determined to be 291 mg KOH/g. As is known in the art ASTM D2896 is a suitable method to determine such. Next, the contribution to TBN from basic soap was determined by titration. A known amount of the detergent was diluted in a 70:28:2 (on a volume basis) of a mixed cyclohexane/IPA/water solvent and digested with 0.5M ethanolic perchloric acid. The resulting solution was titrated with 0.1M KOH solution, which produced two inflection points on the titration curve; EP1 and EP2. Point EP1 can alternatively be used to give TBN from the following equation:

$$\text{Total base number}\left(\frac{\text{mg}KOH}{\text{g}}\right) = \frac{Mw(KOH)*(V_{HClO4}*M_{HClO4} - V_{EP1}*M_{KOH})}{\text{mass}_{Sample}}$$

The second inflection point, EP2, relates to the neutralization of acids produced by the digestion with perchloric acid. The content of basic soap is then calculated from the following equation:

$$\text{Basic Soap}\left(\frac{\text{mg}KOH}{\text{g}}\right) = \frac{(V_{EP2} - V_{EP1})*M_{KOH}*Mw_{KOH}}{\text{mass}_{Sample}}$$

An average of two titrations gave a value for the basic soap content of Example A4 of 50 mg KOH/g.

Next, the amount of carbonate in the detergent sample was determined. An absorption solution consisting of thymol blue indicator, monoethanolamine, de-ionized water and dimethylformamide was prepared. A known amount of the detergent sample was then digested in a 2M HCl/toluene mixture and the liberated carbon dioxide passed through the absorption solution. Titration with tertra-butyl ammonium hydroxide (TBAOH) provided an end-point, confirmed by the change in color of the indicator. The percentage of carbonate in the detergent sample was calculated thus:

$$\% \text{ Carbonate} = \frac{(V_{EP2} + (V_{TBAOH\ added\ in\ 1st\ titration} - V_{EP1})*M_{TBAOH}*Mw_{CO3}}{\text{mass}_{sample}*10},$$

wherein, $Mw_{CO3}$ is the molecular weight of the carbonate ion. The contribution to TBN attributable to carbonate is then calculated from:

$$\text{Metal carbonate (mg}KOH/\text{g)} = \frac{\%\text{Carbonate}*2*10}{Mw_{CO3}}$$

For Example A4, contribution to TBN attributable to carbonate was 91 mg KOH/g. Simple arithmetic then gives the contribution to TBN attributable to borate via:

borate(mg KOH/g)=TBN(mg KOH/g)–basic soap(mg KOH/g)–carbonate(mg KOH/g)

so borate (mg KOH/g) for Example A4 was: 291–50–91=150 mg KOH/g, and mass ratio of borate: carbonate was 150/91=1.6.

The same conventional laboratory procedures were used to determine the mass ratio of borate:carbonate for all other Examples.

Example A5 was similar to Example A4, except the aim was to attain a higher boron content. Thus, in Example A5, a reactor flask was charged with ~395 g of overbased (carbonated) calcium salicylate having the same TBN of ~350 mg KOH/g, soap content over 500 mmol/kg, and basicity index of ~6, ~395 g of xylene, and ~204 g of methanol. The mixture was heated to ~40° C. with stirring, and, under nitrogen, ~241 g of boric acid was added over approximately 1 hour. The temperature was then raised to ~140° C. over ~135 more minutes. The reaction mixture was then cooled to below ~100° C. before diluting with an additional ~262 g of xylene, and then cooling was continued. After cooling, the mixture was centrifuged and concentrated in vacuo on a rotary evaporator at ~140° C. over ~2 hours (to remove diluents, reaction water, and other volatile components) to yield a borated overbased calcium salicylate product. ICP analysis (measured according to ASTM D4951) showed the product to have ~5.7% boron and ~10.2% calcium by mass. The borated product had a TBN (measured according to ASTM D2896) of ~285 mg KOH/g and a basicity index (metal ratio) of ~5.89. The product had a ratio of soap content to mass % boron of 75 mmol/kg; a soap content of 429 mmol/kg; a mass ratio of borate to carbonate of 3.0; a boron content of 5.7 mass % and a calcium content of 10.2 mass %. The hydrocarbyl substitution of the product comprised a mixture of 14 to 18 carbon atoms.

Example A6 was similar to Examples A4 and A5, except the aim was to attain a slightly lower boron content. Thus, in Example A6, a reactor flask was charged with ~500 g of overbased (carbonated) calcium salicylate having the same TBN of ~350 mg KOH/g, soap content over 500 mmol/kg, and basicity index of ~6, ~395 g of xylene, and ~105 g of methanol. The mixture was heated to ~40° C. with stirring, and, under nitrogen, ~113 g of boric acid was added over approximately 1 hour. The temperature was then raised to ~140° C. over ~135 more minutes. The reaction mixture was then cooled to below ~100° C. before diluting with an additional ~151 g of xylene, and then cooling was continued. After cooling, the mixture was centrifuged and concentrated in vacuo on a rotary evaporator at ~140° C. over ~2 hours (to remove diluents, reaction water, and other volatile components) to yield a borated overbased calcium salicylate product. ICP analysis (measured according to ASTM D4951) showed the product to have ~3.8% boron and ~11.6% calcium by mass. The borated product had a TBN (measured according to ASTM D2896) of ~314 mg KOH/g and a basicity index (metal ratio) of ~5.72. The product had a ratio of soap content to mass % boron of 123 mmol/kg; a soap content of 469 mmol/kg; and a mass ratio of borate to carbonate of 0.8. The hydrocarbyl substitution of the product comprised a mixture of 14 to 18 carbon atoms.

Example A7 was similar to Example A6, except the aim was to attain an even lower boron content. Thus, in Example A7, a reactor flask was charged with ~1.5 kg of overbased (carbonated) calcium salicylate having the same TBN of ~350 mg KOH/g, soap content over 500 mmol/kg, and basicity index of ~6, ~1185 g of xylene, and ~316 g of methanol. The mixture was heated to ~40° C. with stirring, and, under nitrogen, ~340 g of boric acid was added over approximately 1 hour. The temperature was then raised to ~140° C. over ~135 more minutes. The reaction mixture was then cooled to below ~100° C. before diluting with an additional ~452 g of xylene, and then cooling was continued. After cooling, the mixture was centrifuged and concentrated in vacuo on a rotary evaporator at ~140° C. over ~2 hours (to remove diluents, reaction water, and other volatile components) to yield a borated overbased calcium salicylate product. ICP analysis (measured according to ASTM D4951) showed the product to have ~3.6% boron and ~11.8% calcium by mass. The borated product had a TBN (measured according to ASTM D2896) of ~312 mg KOH/g and a basicity index (metal ratio) of ~5.81. The product had a ratio of soap content to mass % boron of 133 mmol/kg; and a soap content of 480 mmol/kg. The hydrocarbyl substitution of the product comprised a mixture of 14 to 18 carbon atoms.

Example A8 was similar to Examples A4, A5, A6, and A7, except that ~900 g of a different overbased (carbonated) calcium salicylate, having the same TBN of ~350 mg KOH/g, but a different soap content below 400 mmol/kg and a different basicity index of ~8, was charged into the reactor flask with ~711 g of xylene and ~195 g of methanol. The mixture was heated to ~40° C. with stirring, and, under nitrogen, ~217 g of boric acid was added over approximately 1 hour. The temperature was then raised to ~140° C. over ~135 more minutes. The reaction mixture was then cooled to below ~100° C. before diluting with an additional ~273 g of xylene, and then cooling was continued. After cooling, the mixture was centrifuged and concentrated in vacuo on a rotary evaporator at ~140° C. over ~2 hours (to remove diluents, reaction water, and other volatile components) to yield a borated overbased calcium salicylate product. ICP analysis (measured according to ASTM D4951) showed the product to have ~3.9% boron and ~11.9% calcium by mass. The borated product had a TBN (measured according to ASTM D2896) of ~310 mg KOH/g and a basicity index (metal ratio) of ~7.95. The product had a ratio of soap content to mass % boron of 89 mmol/kg; a soap content of 348 mmol/kg; and a mass ratio of borate to carbonate of 0.8. The hydrocarbyl substitution of the product comprised a mixture of 14 to 18 carbon atoms.

Comparative Example A9 was similar to Example A8, except that ~901 g of a different overbased (carbonated) calcium salicylate, having a TBN of ~225 mg KOH/g, a soap content above 600 mmol/kg, and a basicity index of ~3, was charged into the reactor flask with ~711 g of xylene and ~111 g of methanol. The mixture was heated to ~40° C. with stirring, and, under nitrogen, ~106 g of boric acid was added over approximately 1 hour. The temperature was then raised to ~140° C. over ~135 more minutes. The reaction mixture was then cooled to below ~100° C. before diluting with an additional ~257 g of xylene, and then cooling was continued. After cooling, the mixture was centrifuged and concentrated in vacuo on a rotary evaporator at 140° C. over ~2 hours (to remove diluents, reaction water, and other volatile components) to yield a borated overbased calcium salicylate product. ICP analysis (measured according to ASTM D4951) showed the product to have ~1.7% boron and ~7.1% calcium by mass. The borated product had a TBN (measured according to ASTM D2896) of ~212 mg KOH/g and a basicity index (metal ratio) of ~3.56. The product had a ratio of soap content to mass % boron of 359 mmol/kg; a soap content of 611 mmol/kg; and a mass ratio of borate to carbonate of 1.3. The hydrocarbyl substitution of the product comprised a mixture of 14 to 18 carbon atoms.

Comparative Example A10 was similar to Example A9, except that ~1 kg of the same overbased (carbonated) calcium salicylate, having a TBN of ~225 mg KOH/g, a soap content above 600 mmol/kg, and a basicity index of ~3, was charged into the reactor flask with ~790 g of xylene and ~188 g of methanol. The mixture was heated to ~40° C. with stirring, and, under nitrogen, ~185 g of boric acid was added over approximately 1 hour. The temperature was then raised to ~140° C. over ~135 more minutes. The reaction mixture was then cooled to below ~100° C. before diluting with an additional ~337 g of xylene, and then cooling was continued. After cooling, the mixture was centrifuged and concentrated in vacuo on a rotary evaporator at 140° C. over ~2 hours (to remove diluents, reaction water, and other volatile components) to yield a borated overbased calcium salicylate product. ICP analysis (measured according to ASTM D4951) showed the product to have ~2.9% boron and ~7.5% calcium by mass. The borated product had a TBN (measured according to ASTM D2896) of ~202 mg KOH/g and a basicity index (metal ratio) of ~3.01. The product had a ratio of soap content to mass % boron of 206 mmol/kg; a soap content of 597 mmol/kg; and a mass ratio of borate to carbonate of 2.1. The hydrocarbyl substitution of the product comprised a mixture of 14 to 18 carbon atoms.

In Comparative Example A11, a reactor flask was charged with ~606 g of approximately neutral calcium salicylate having a TBN of ~64 mg KOH/g, a soap content over 500 mmol/kg, and a basicity index of ~6, —500 g of xylene, ~130 g of methanol, and ~23 g of water. The mixture was heated to ~40° C. with stirring, and, under nitrogen, ~178 g of boric acid was added over approximately 1 hour. The temperature was then raised to ~140° C. over ~135 more minutes. During the temperature ramp, when the temperature reached ~60° C., an additional ~284 g of a Group I lubricating oil basestock having a KV100 of ~5 cSt. The reaction mixture was then cooled, followed by centrifugation and concentration in vacuo on a rotary evaporator at ~140° C. over ~2 hours (to remove diluents, reaction water, and other volatile components) to yield a borated calcium salicylate product. ICP analysis (measured according to ASTM D4951) showed the product to have ~1.8% boron and ~2.3% calcium by mass. The borated product had a TBN (measured according to ASTM D2896) of ~60 mg KOH/g and a basicity index (metal ratio) of ~1.21. The product had a ratio of soap content to mass % boron of 234 mmol/kg; and a soap content of 421 mmol/kg. The hydrocarbyl substitution of the product comprised a mixture of 14 to 18 carbon atoms.

In Example A12, a reactor flask was charged with ~1000 g of overbased (carbonated) magnesium salicylate having a TBN of ~340 mg KOH/g, a soap content over 400 mmol/kg, and a basicity index of ~7.5, ~790 g of xylene, and ~233 g of methanol. The mixture was heated to ~40° C. with stirring, and, under nitrogen, ~183 g of boric acid was added over approximately 1 hour. The temperature was then raised to ~140° C. over ~135 more minutes. The reaction mixture was then cooled to below ~100° C. before diluting with an additional ~337 g of xylene, and then cooling was continued. After cooling, the mixture was centrifuged and concentrated in vacuo on a rotary evaporator at ~140° C. over ~2 hours (to remove diluents, reaction water, and other volatile components) to yield a borated overbased magnesium salicylate product. ICP analysis (measured according to ASTM D4951) showed the product to have ~1.7% boron and ~7.2% magnesium by mass. The borated product had a TBN (measured according to ASTM D2896) of ~301 mg KOH/g and a basicity index (metal ratio) of ~6.71. The product had a ratio of soap content to mass % boron of 240 mmol/kg; a soap content of 408 mmol/kg; and a mass ratio of borate to carbonate of 1.3. The hydrocarbyl substitution of the product comprised a mixture of 14 to 18 carbon atoms.

In Example A13, a reactor flask was charged with ~800 g of overbased (carbonated) calcium salicylate having the same TBN of ~350 mg KOH/g, a soap content over 500 mmol/kg, and a basicity index of ~6, and ~458 g of xylene. The mixture was heated to ~80° C. with stirring, and, under nitrogen, a mixture of ~191 g of boric acid in ~1104 g methanol was added over approximately 1 hour. During the addition, some distillation of solvent was observed. The temperature was then raised to ~140° C. over ~45 more minutes. The reaction mixture was then cooled to below ~100° C. before diluting with an additional ~668 g of xylene, and then cooling was continued. After cooling, the mixture was centrifuged and concentrated in vacuo on a rotary evaporator at ~140° C. over ~2 hours (to remove diluents, reaction water, and other volatile components) to yield a borated overbased calcium salicylate product. ICP analysis (measured according to ASTM D4951) showed the product to have ~3.0% boron and ~11.3% calcium by mass. The borated product had a TBN (measured according to ASTM D2896) of ~308 mg KOH/g and a basicity index (metal ratio) of ~5.8. The product had a ratio of soap content to mass % boron of 164 mmol/kg; and a soap content of 487 mmol/kg. The hydrocarbyl substitution of the product comprised a mixture of 14 to 18 carbon atoms.

Additive Package Stability—Borated vs. Unborated Detergents

To test the effect of detergent boration on package stability, variations on a passenger car motor oil (PCMO) addpack were made. In addition, because of well-known addpack-destabilizing interactions between salicylate-based detergents and certain organic components (loosely categorized as ashless organic friction modifiers, for simplicity), usually unstable combinations of salicylate-based detergents and said ashless organic friction modifiers were also tested to probe the effects of detergent boration.

Package stability was tested as defined herein, by exposing samples to at ~60° C. in air in an oven for at least 12 weeks—data shown in the table below includes observations from weeks 0 (initial), 4, 7, and 12. Initial testing at week 0 was accomplished at room temperature (~20-25° C.), while all other data points were done after the requisite number of weeks sitting in an oven at ~60° C. In that table below, "CB" means clear and bright, "SH" means slightly hazy; "H" means hazy; "VH" means very hazy; "F" means flocculate, usually accompanied by a percentage (the larger the percentage, the more extensive the floc); "PS" means phase separation, usually accompanied by a percentage (the larger the percentage, the more extensive the phase separation); "G" means gel, usually accompanied by a percentage (the larger the percentage, the more extensive the gelation); "tsed" means trace sediment; and "MTS" means minor sediment.

For Examples and Comparative Examples B1-B12, the base additive package contained a mixture of an overbased (unborated) magnesium salicylate and an overbased (unborated) calcium salicylate detergent component, a mixture of borated PIBSA-PAM and unborated PIBSA-PAM dispersant components, a zinc-containing antiwear component, a combination of aromatic amine and hindered phenol antioxidant components, a benzotriazole corrosion inhibitor component, a tackifier component, an anti-foamant component, and a diluent/basestock. Additive package components may be essentially pure (little to no diluent) or may encapsulate an active ingredient in diluted form, sometimes containing as much as 60% diluent/inactive ingredient.

To probe stability issues, the base additive package was modified in various ways, most notably to add and/or to substitute overbased or borated and overbased calcium salicylate component(s), to add ashless organic friction modifiers, or both. In this series, when detergents were added, they were substituted for each other to achieve roughly equal molar amounts of alkaline earth metal (e.g., where a calcium salicylate was substituted for a magnesium salicylate) or to achieve roughly equal molar amounts of a particular alkaline earth metal (e.g., where a borated calcium salicylate was substituted for an unborated calcium salicylate in a higher amount to achieve a roughly equal calcium content). Because the ashless organic friction modifiers were not originally present in the base additive package, they were merely added, not substituted for any other component (even diluent component). In this series, the unmodified additive package component amounts were kept the same, but the treat rate was adjusted to account for the difference in addpack amount resulting from the substitutions/additions, such that fully formulated lubricating oil compositions made by diluting the additive packages with additional diluent/basestock (and optionally other components) contained similar contents (again, with the exception of ashless organic friction modifiers) of metals, phosphorus, sulfur (but not boron, which is additionally present in borated detergents, and also not oxygen and optionally also not nitrogen, which are present in the ashless organic friction modifiers), detergent(s), dispersant(s), antiwear agent, antioxidant(s), corrosion inhibitor, tackifier, and anti-foamant.

TABLE 1

| ~60° C. Stability | Comp Ex B1 | Comp Ex B2 | Example B3 | Example B4 |
| --- | --- | --- | --- | --- |
| week 0 | CB | CB | SH | VH |
| week 4 | tsed, CB | tsed, CB | 0.05% G, SH | tsed, H |
| week 7 | tsed, CB | tsed, CB | 0.10% G, SH | tsed, H |
| week 12 | tsed, CB | tsed, CB | 0.20% G, H | tsed, H |

In Table 1 above, Comparative Example B1 utilizes the overbased (carbonated but unborated) calcium salicylate detergent used as a reactant in Examples A4-A7 above, which exhibits a relatively high soap content, while Comparative Example B2 utilizes the overbased (carbonated but unborated) calcium salicylate detergent used as a reactant in Example A8 above, which exhibits a lower soap content. Both detergent components have approximately the same TBN. Examples B3 and B4 are identical to Comparative Examples B1 and B2, respectively, except that the former additionally contain a glycerol monooleate friction modifier component (which can comprise a reaction product of ~1.5 equivalent of oleic acid and ~1 equivalent of glycerol).

As can be seen from the package stability results in Table 1, the calcium salicylate detergents of Comparative Examples B1 and B2 show comparable stability in the additive package, but the addition of the ashless organic friction modifier in Examples B3 and B4 seems to show package instability in both cases (whether as gelation or haze).

TABLE 2

| ~60° C. Stability | Example B5 | Example B6 | Example B7 | Example B8 |
|---|---|---|---|---|
| week 0 | CB | VH* | SH | VH |
| week 4 | tsed, CB | tsed, CB | tsed, SH | 8% F, SH |
| week 7 | tsed, CB | tsed, CB | tsed, CB | 4-6% F, CB |
| week 12 | tsed, CB | tsed, CB | tsed, CB | 4-6% F, 10% haze |

*Package was very hazy when received (room temp) but cleared quickly upon exposure to ~60° C.

In Table 2 above, Examples B5 and B6 utilize borated versions of the overbased calcium salicylate detergents of Comparative Examples B1 and B2 (the borated products of Examples A7 and A8), respectively. Analogous to Examples B3 and B4 in Table 1, Examples B7 and B8 in Table 2 are identical to Examples B5 and B6, except that the former additionally contain a glycerol monooleate friction modifier component (which comprises a reaction product of ~1.5 equivalent of oleic acid and ~1 equivalent of glycerol).

As can be seen from the package stability results, the borated salicylate detergents of Examples B5 and B6 show approximately comparable stability to each other in the additive package in Table 2, as well as comparable stability to their unborated analogs in Comparative Examples B1 and B2 from Table 1. However, unlike in Table 1, Table 2 shows a differential result when the ashless organic friction modifier is added to the borated salicylate detergents. The borated analog of the lower soap content salicylate in Example B8 actually appeared worse (based on heavy floc content throughout and considerable haze at shorter/longer time intervals) than its unborated counterpart in Example B4. But, surprisingly, the borated analog of the relatively high soap content salicylate detergent in Example B7 showed considerably improved package stability relative to its unborated counterpart in Example B3, and perhaps even comparable to the stability of its counterpart in Example B5, in which the salicylate detergent was not combined with the ashless organic friction modifier. As the instability of salicylate detergents and certain ashless organic friction modifiers is well-known, it appears that the boration process unexpectedly adds a package stability credit that can counteract, at least partially if not (almost) entirely the stability debit in combining salicylate detergents and ashless organic friction modifiers.

TABLE 3

| ~60° C. Stability | Example B3 | Example B7 | Example B9 | Example B10 | Example B11 | Example B12 |
|---|---|---|---|---|---|---|
| week 0 | SH | SH | SH | CB | SH | SH |
| week 4 | 0.05% G, SH | tsed, SH | 0.10% G, SH | tsed, CB | tsed, CB | tsed, CB |
| week 7 | 0.10% G, SH | tsed, CB | 0.10% G, SH | tsed, CB | tsed, CB | tsed, CB |
| week 12 | 0.20% G, H | tsed, CB | 0.25% G, SH | tsed, CB | tsed, CB | tsed, CB |

In Table 3, Examples B3 and B7 were the same as in Tables 1 and 2, respectively, reflecting unborated and borated versions of a relatively high soap content calcium salicylate detergent component with glycerol monooleate friction modifier. Examples B9 and B10 reflect the unborated relatively high soap content calcium salicylate with other ashless/organic friction modifiers, specifically tallow esters of triethanolamine (TEEMA) and octadecenyl succinic anhydride (ODSA), respectively. Examples B11 and B12 reflect the borated analogs of the salicylate detergents with the same ashless organic friction modifiers as in Examples B9 and B10, respectively.

As can be seen from the package stability results in Table 3, the packages containing the combination of the borated salicylate and the ashless organic friction modifiers were more stable over time at elevated temperature for Examples B7 and B11, compared to combinations with the unborated salicylate in Examples B3 and B9, respectively. Because the combination of unborated salicylate and TEEMA (Example B10) did not exhibit significant package instability, it should be no surprise that an improvement was not seen for the combination of the borated analog and TEEMA (Example B12). However, it is noted that one might not observe a package stability credit from a borated detergent in an additive package that was not significantly unstable to start with—indeed, the package stability of the borated detergent combination was not appreciably worse than the unborated combination. This indicates both that ashless organic friction modifier-salicylate detergent package instabilities are not necessarily inherent and that additive packages with borated detergents seem to universally exhibit package stability across several different types of ashless organic friction modifiers.

For Examples and Comparative Examples B13-B25, the base additive package contained an overbased (unborated) calcium salicylate detergent component, an unborated PIBSA-PAM dispersant component, a zinc-containing antiwear component, a molybdenum-containing antiwear component, a combination of aromatic amine and hindered phenol antioxidant components, a benzotriazole corrosion inhibitor component, a tackifier component, an anti-foamant component, and a diluent/basestock. Additive package components may be essentially pure (little to no diluent) or may encapsulate an active ingredient in diluted form, sometimes containing as much as 60% diluent/inactive ingredient.

To probe stability issues, the base additive package was modified to add and/or to substitute overbased or borated and overbased detergent component(s). In this series, when detergents were added, they were substituted for each other to achieve roughly equal mass amounts of detergent, on an alkaline earth metal-free basis (e.g., where one calcium salicylate was substituted for another calcium salicylate, where a calcium sulfonate was substituted for a calcium salicylate, or where a borated calcium salicylate was substituted for an unborated calcium salicylate). In this series, the unmodified additive package component amounts were kept the same, but the treat rate was adjusted to account for the difference in addpack amount resulting from the substitutions/additions.

TABLE 4

| ~60° C. Stability | Comp Ex B13 | Comp Ex B14 | Example B15 | Example B16 | Example B17 | Example B18 |
|---|---|---|---|---|---|---|
| week 0  | CB   | CB         | CB   | CB   | CB   | CB   |
| week 4  | tsed | <0.05% PS  | tsed | tsed | tsed | tsed |
| week 7  | tsed | <0.05% PS  | tsed | tsed | tsed | tsed |
| week 12 | tsed | <0.05% PS  | MTS  | MTS  | tsed | tsed |

In Table 4 above, Comparative Example B13 utilizes the overbased (carbonated but unborated) calcium salicylate detergent used as a reactant in Example A8 above, which contained a lower (intermediate) soap content, while Comparative Example B14 utilizes the overbased (carbonated but unborated) calcium salicylate detergent used as a reactant in Examples A4-A7 above, which contained a relatively high soap content. Both unborated detergent components had approximately the same TBN. Examples B15, B16, and B17, are identical to Comparative Example B14, except that the over based borated detergent products of Examples A4-A6, respectively, were substituted for the unborated detergent. Example B18 utilizes the borated overbased calcium salicylate detergent product from Example A8 above (analog to its unborated counterpart reproduced in Comparative Example B13).

As can be seen from the package stability results in Table 4, sometimes unborated overbased calcium salicylate detergents can exhibit minor stability issues in additive packages containing molybdenum-containing antiwear agents, even in the absence of ashless OFMs (Comparative Example B14). However, the borated calcium salicylate detergents of Examples B15-B17 show comparable and acceptable stability in the additive package, relative to Comparative Example B13, and in contrast to their unborated detergent analog from Comparative Example B14.

TABLE 5

| ~60° C. Stability | Comp Ex B13 | Comp Ex B19 | Comp Ex B20 | Comp Ex B21 |
|---|---|---|---|---|
| week 0  | CB   | CB       | CB        | CB       |
| week 4  | tsed | 0.15% PS | <0.05% PS | 0.15% PS |
| week 7  | tsed | 0.20% PS | <0.05% PS | 0.20% PS |
| week 12 | tsed | 0.20% PS | <0.05% PS | 0.15% PS |

In Table 5 above, Comparative Example B19 utilizes the overbased (carbonated but unborated) calcium salicylate detergent used as a reactant in Comparative Examples A9 and A10 above, with a very high soap content, while Comparative Examples B20 and B21 utilize the analogous borated overbased calcium salicylate detergent products from Comparative Examples A9 and A10, respectively.

As can be seen from the package stability results in Table 5, while boration can help improve package instability in some circumstances, boration does not universally improve package stability. A relatively unstable unborated detergent (Comparative Example B19) can have its stability improved a little, but not completely, by boration under certain conditions (in the case of Comparative Example B20), but not in all conditions (in the case of Comparative Example B21), even in very high soap content situations. The basicity index of the unborated and borated detergents in Comparative Examples B19-B21 is from 2.9-3.0. As noted in Table 4, the relatively low soap content and relatively high basicity index calcium salicylate detergents of Comparative Example B13 and Example B18 (unborated and borated, respectively) both exhibit comparable and acceptable package stability, while the relatively high soap content and lower basicity index calcium salicylate detergents of Comparative Examples B19-B21 in Table 5 universally exhibit inferior package stability. Without being bound by theory, it surprisingly seems that basicity index may be of relatively higher importance than soap content in managing issues regarding package stability, at least when doing so via detergent boration.

TABLE 6

| ~60° C. Stability | Comp Ex B22 | Example B23 | Comp Ex B24 | Comp Ex B25 |
|---|---|---|---|---|
| week 0  | CB   | CB   | CB   | 0.05% PS |
| week 4  | tsed | tsed | tsed | 0.05% PS |
| week 7  | MTS  | MTS  | tsed | 0.05% PS |
| week 12 | MTS  | MTS  | tsed | 0.05% G  |

In Table 6 above, Comparative Example B22 utilizes the overbased (carbonated but unborated) magnesium salicylate detergent used as a reactant in Example A12 above, while Example B23 utilizes the analogous borated overbased magnesium salicylate detergent product from Example A12 above. Comparative Examples B24 and B25 utilized an overbased (carbonated but unborated) calcium sulfonate detergent (~300 mg KOH/g TBN, less than 250 mmol soap content, and basicity index of ~14) and its borated analog, respectively. Although the method of boration of this calcium sulfonate detergent was not specifically described herein, it was done using similar procedures and under similar conditions to those detailed for salicylate detergents (both inventive and comparative) herein.

In Table 6, Comparative Example B22 and Example B23 show similar behavior to Comparative Example B13 and Example B14—neither overbased salicylate detergent started with significant package stability issues, and boration did not cause any package stability issues to develop. The case is different with calcium sulfonate, however. Even in the situation where the unborated overbased calcium sulfonate was relatively package-stable (Comparative Example B24), the borated version showed significant gelation (Comparative Example B25), even upon initial additive package blending (week 0). Other unpublished data indicates that boration, according to the processes described herein, seem to actually introduce package instability in overbased alkaline earth metal sulfonates, where there would not otherwise be package instability. Although there are many other potential actions available to the skilled artisan in attaining package stability besides borating a detergent, the repeated negative results with sulfonate detergents may indicate a more fundamental difficulty with boration vis-à-vis maintaining package stability of sulfonate detergents.

Performance of Formulated Additive Packages Containing Borated Salicylates

Comparative Examples $C_1$-$C_4$ correspond to inventive Examples 1-4 from Table 1 of U.S. Patent Publication No. 2015/0005208 A1 to JX Nippon (the '208 publication). Paragraphs [0147]-[0149] of the '208 publication described the Driving Valve System Monitoring Friction Test in which friction torques were measured at oil temperatures of ~100° C. and at ~350 rpm. Normalization was done in the '208 publication relative to Comparative Example B2, but, while its inventive Examples 1-4 showed a range of ~3.0-9.5% friction torque improvement rate, it should be noted that the boron-free salicylate detergent-containing composition of its Comparative Example 1 showed a ~6.9% torque improvement. If one were to measure friction torque improvement in the '208 publication relative to its boron-free Comparative Example 1 instead, its higher boron content formulations (inventive Examples 3-4) would appear to worsen friction torque, while its lower boron content formulations (inventive Examples 1-2) would show only modest improvements. As increasing boron content is believed to enable friction torque improvement, this seems like quite a confusing result. Without being bound by theory, it is hypothesized that the higher boron content detergents in the '208 publication contain boron species that are less available/unavailable or that are in a chemical form that cannot sufficiently contribute to the frictional tribofilm surface.

Notably, paragraphs [0075]-[0076] of the '208 publication teaches not only that lubricant compositions containing detergent metal ratios higher than 3.3 are undesirable, as they tend to reduce friction torque behavior, but also that the highest preference is for a detergent metal ratio of 1.9 or less (with a lower limit of 1.01, to account for formulation lubricity and engine "startability"). It should not be lost on the reader of the '208 publication that only its inventive Example 1 satisfies that most preferable metal ratio, nor that the same composition has the highest measured friction torque value, as normalized.

Although not a direct comparison, Example C5 utilized an additive package composition containing similar components to Example B5, including a borated and overbased calcium salicylate according to the present disclosure (made according to Example A13). In order to assess friction torque, similarly to the '208 publication, Comparative Example C6 utilized an analogous additive package composition to Example C5, except with an unborated but overbased calcium salicylate. The relative formulation measurements are shown in Table 7 below—"detergent boron content" should be understood to refer to the amount of boron in the final formulation due solely to the borated detergent component.

TABLE 7

| Property | Comp Ex C6 | Example C5 |
|---|---|---|
| detergent boron content | 0 | ~0.015 |
| KV40 | ~26.4 | ~26.9 |
| KV100 | ~6.19 | ~6.19 |

TABLE 7-continued

| Property | Comp Ex C6 | Example C5 |
|---|---|---|
| HTHS100 | ~4.5 | ~4.5 |
| HTHS150 | ~2.3 | ~2.3 |
| torque reduction | — | ~11.5% |

In Comparative Example C6 and Example C5, friction torque reduction was measured at ~80° C. and at ~650 rpm engine rate. Torque reduction in Table 7 was normalized by the Comparative Example C6 formulation. Although different conditions than were used in the '208 publication, it should be understood that both lower boron content and test temperature (in both sets of regimes, encompassed by all collective measurements) typically (and usually drastically) reduce the absolute value of torque reduction. As such, although a quantitative assessment at equal conditions and in identical formulation space is not available, it is believed that the relatively large torque reduction shown by the borated calcium salicylate-containing formulation of Example C5, relative to its otherwise identical unborated calcium salicylate-containing formulation of Comparative Example C6, is both surprising and unexpected.

All documents described herein are incorporated by reference herein, including any priority documents and/or testing procedures, to the extent they are not inconsistent with this text. As should be apparent from the foregoing general description and the specific embodiments, while forms of the present disclosure have been illustrated and described, various modifications can be made without departing from the spirit and scope of the inventive disclosure. Accordingly, it is not intended that the invention be necessarily limited thereby.

What is claimed is:

1. An overbased alkaline earth metal hydrocarbyl-substituted salicylate detergent comprising both carbonate and borate moieties and exhibiting the following characteristics:
   a basicity index of at least 3.8;
   a ratio of soap content to mass % boron is greater than 55 mmol/kg;
   a soap content of at least 330 mmol/kg and less than or equal to 500 mmol/kg;
   a TBN, measured according to ASTM D2896, of at least 220 mg KOH/g; and
   a mass ratio of borate to carbonate from 0.75 to 6.0,
   wherein the alkaline earth metal comprises calcium and/or magnesium, and the hydrocarbyl substitution comprises 9 to 30 carbon atoms.

2. An overbased calcium salicylate detergent according to claim 1, wherein all four of the following are satisfied:
   the basicity index is not greater than 9.0;
   the ratio of soap content to mass % boron is less than 300 mmol/kg;
   the TBN, measured according to ASTM D2896, is at most 500 mg KOH/g; and
   the hydrocarbyl substitution comprises a $C_{14}$ to $C_{24}$ alkyl or alkenyl moiety.

3. An overbased calcium salicylate detergent according to claim 1, which exhibits a boron content, according to ASTM D4951, of at least 3.2% by mass.

4. An overbased calcium salicylate detergent according to claim 1, wherein the mass ratio of borate to carbonate is from 1.0 to 5.0.

5. An overbased calcium salicylate detergent according to claim 1, which exhibits an alkaline earth metal content, according to ASTM D4951, of at least 7.0% by mass.

6. An overbased calcium salicylate detergent according to claim 1, which exhibits a mass ratio of alkaline earth metal to boron is from 1.5 to 5.5.

7. An overbased calcium salicylate detergent according to claim 1, wherein:
the basicity index is from 5.0 to 8.3;
the ratio of soap content to mass % boron is between 70 and 275 mmol/kg;
the TBN, measured according to ASTM D2896, is from 265 to 350 mg KOH/g;
the combined calcium and magnesium content, according to ASTM D4951, is from 7.0% to 12.5% by mass;
the boron content, according to ASTM D4951, is from 3.5% to 6.8% by mass;
the soap content is from 350 to 500 mmol/kg;
the mass ratio of alkaline earth metal to boron is from 1.7 to 4.5;
the mass ratio of borate to carbonate moieties is from 1.6 to 3.0; and
the hydrocarbyl substitution comprises a $C_{14}$ to $C_{19}$ alkyl or alkenyl moiety.

8. A method for making a package-stable overbased alkaline earth metal hydrocarbyl-substituted salicylate detergent comprising both carbonate and borate moieties, the method comprising the steps of:
providing an oil-soluble or oil-dispersible overbased but unborated alkaline earth metal hydrocarbyl-substituted salicylate detergent made by reacting a mineral oil solution of an acid with a stoichiometric excess of a neutralizing agent comprising an alkaline earth metal carbonate or bicarbonate, optionally in the presence of promoter, at a temperature from 60 to 200° C. for a sufficient period of time to have thereby formed the overbased but unborated alkaline earth metal hydrocarbyl-substituted salicylate detergent, which exhibits a basicity index of at least 3.5, a soap content of at least 330 mmol/kg and less than or equal to 500 mmol/kg, an alkaline earth metal content, measured according to ASTM D4951, of at least 7.0% by mass, and a TBN, according to ASTM D2896, of at least 240 mg KOH/g, wherein the alkaline earth metal comprises calcium and/or magnesium, wherein the overbased but unborated alkaline earth metal hydrocarbyl-substituted salicylate detergent comprises carbonate moieties, and wherein the hydrocarbyl substitution comprises 9 to 30 carbon atoms;
admixing said overbased but unborated alkaline earth metal hydrocarbyl-substituted salicylate detergent in an organic diluent medium comprising an aprotic hydrocarbon solvent and a $C_1$-$C_4$ primary alcohol but comprising no intentionally added water with a boron source at a temperature below 100° C. to form a reaction mixture;
heating the reaction mixture to a temperature from 105° C. to 225° C. at a heating rate below 3° C./min in a borating process to form a crude borated detergent product;
optionally, further adding additional aprotic hydrocarbon solvent, thereby still forming a crude borated detergent product; and
removing a significant portion of the diluent medium, as well as water, formed during the borating process, in order to form the overbased alkaline earth metal hydrocarbyl-substituted salicylate detergent according to claim 1.

9. The method according to claim 8, wherein:
the aprotic hydrocarbon solvent comprises benzene, xylene, toluene, mesitylene, naphthalene, cyclohexane, cyclooctane, heptane, octane, decane, dodecane, or a combination thereof; and
the boron source comprises orthoboric acid, metaboric acid, tetraboric acid, monoammonium borate, diammonium borate, triammonium borate, $C_1$-$C_4$ alkyl dihydrogen borate, di-$C_1$-$C_4$ alkyl hydrogen borate, tri-$C_1$-$C_4$ alkyl borate, or a combination thereof.

10. A lubricant additive package concentrate comprising:
less than 40% by mass of a Group I, Group II, and/or Group III lubricating oil basestock;
at least 0.5% by mass of the boron-containing overbased calcium salicylate detergent according to claim 1;
at least one ashless dispersant;
at least one antioxidant;
at least one friction modifier; and
optionally, one or more of an additional detergent, a corrosion inhibitor, an antiwear agent, a seal swelling agent, an anti-foamant, an extreme pressure agent, a viscosity modifier, and a pour point depressant.

11. A lubricant additive package concentrate according to claim 10, wherein the at least one friction modifier comprises a substantially sulfur-free ashless organic friction modifier.

12. A lubricant additive package concentrate according to claim 10, wherein the at least one friction modifier comprises a substantially nitrogen-free and substantially sulfur-free ashless organic friction modifier.

13. A lubricant additive package concentrate according to claim 10, which exhibits package stability at −60° C. for at least 12 weeks.

14. A lubricating oil composition comprising:
at least 70% by mass of a lubricating oil basestock comprising one or more of Group I, Group II, Group III, and/or Group IV basestocks; and
at least 5% by mass of the lubricant additive package concentrate according to claim 10.

15. A lubricating oil composition comprising:
at least 85% by mass of a lubricating oil basestock comprising one or more of Group I, Group II, Group III, and/or Group IV basestocks;
at least 0.05% by mass of the boron-containing overbased calcium salicylate detergent according to claim 1;
at least one ashless dispersant;
at least one antioxidant;
at least one friction modifier; and
optionally, one or more of an additional detergent, a corrosion inhibitor, an antiwear agent, a seal swelling agent, a tackifier, a demulsifier, an anti-foamant, an extreme pressure agent, a viscosity modifier, and a pour point depressant.

16. A lubricating oil composition comprising:
at least 85% by mass of a lubricating oil basestock comprising one or more of Group I, Group II, Group III, and/or Group IV basestocks;
at least 0.05% by mass of the boron-containing overbased calcium salicylate detergent made according to the method of claim 8;
at least one ashless dispersant;
at least one antioxidant;
at least one friction modifier; and
optionally, one or more of an additional detergent, a corrosion inhibitor, an antiwear agent, a seal swelling agent, a tackifier, a demulsifier, an anti-foamant, an extreme pressure agent, a viscosity modifier, and a pour point depressant.

17. The method of claim 8, wherein the overbased alkaline earth metal hydrocarbyl-substituted salicylate detergent produced by claim 8, exhibits package stability at −60° C. for at least 12 weeks.

18. A lubricant additive package concentrate comprising:
- less than 40% by mass of a Group I, Group II, and/or Group III lubricating oil basestock;
- at least 0.5% by mass of the boron-containing overbased calcium salicylate detergent made according to the method of claim 8;
- at least one ashless dispersant;
- at least one antioxidant;
- at least one friction modifier; and
- optionally, one or more of an additional detergent, a corrosion inhibitor, an antiwear agent, a seal swelling agent, an anti-foamant, an extreme pressure agent, a viscosity modifier, and a pour point depressant.

19. A lubricant additive package concentrate according to claim 18, wherein the at least one friction modifier comprises a substantially sulfur-free ashless organic friction modifier.

20. A lubricant additive package concentrate according to claim 18, wherein the at least one friction modifier comprises a substantially nitrogen-free and substantially sulfur-free ashless organic friction modifier.

21. A lubricant additive package concentrate according to claim 18, which exhibits package stability at −60° C. for at least 12 weeks.

\* \* \* \* \*